US009575075B2

United States Patent
Leveillard et al.

(10) Patent No.: US 9,575,075 B2
(45) Date of Patent: Feb. 21, 2017

(54) METHODS FOR TREATING CONE DYSTROPHY WITH NEURONAL VIABILITY FACTOR, RDCVF2

(75) Inventors: Thierry Leveillard, Maison Alfort (FR); José-Alain Sahel, Paris (FR); Céline Jaillard, Antony (FR); Olivier Poch, Strasbourg (FR)

(73) Assignees: INSERM (Institut National de la Sante et Recherche Medicale), Paris (FR); Centre National de la Recherche Scientifique (CNRS), Paris (FR)

( * ) Notice: Subject to any disclaimer, the term of this patent is extended or adjusted under 35 U.S.C. 154(b) by 1414 days.

(21) Appl. No.: 12/602,736

(22) PCT Filed: Jun. 5, 2008

(86) PCT No.: PCT/EP2008/057031
§ 371 (c)(1),
(2), (4) Date: Jun. 1, 2010

(87) PCT Pub. No.: WO2008/148860
PCT Pub. Date: Dec. 11, 2008

(65) Prior Publication Data
US 2010/0247496 A1 Sep. 30, 2010

(30) Foreign Application Priority Data
Jun. 5, 2007 (EP) .................................. 07109652

(51) Int. Cl.
| | | |
|---|---|---|
| A61K 38/00 | (2006.01) |
| A61K 49/00 | (2006.01) |
| A61K 38/18 | (2006.01) |
| C07K 14/475 | (2006.01) |
| C07K 14/48 | (2006.01) |
| C07K 14/00 | (2006.01) |
| A61K 38/16 | (2006.01) |
| G01N 33/68 | (2006.01) |
| A61K 38/44 | (2006.01) |
| C07K 14/435 | (2006.01) |

(52) U.S. Cl.
CPC ......... *G01N 33/6896* (2013.01); *A61K 38/44* (2013.01); *C07K 14/00* (2013.01); *C07K 14/435* (2013.01); *G01N 2800/2821* (2013.01); *G01N 2800/2835* (2013.01)

(58) Field of Classification Search
CPC ...... C07K 14/00; C07K 14/435; C07K 14/47; G01N 33/6896; G01N 33/5058; A61K 2300/00; A61K 38/1709; A61K 38/57; A61K 9/0048; A61F 2009/00863; A61F 9/0026
See application file for complete search history.

(56) References Cited

U.S. PATENT DOCUMENTS

| | | | | |
|---|---|---|---|---|
| 7,795,387 | B2 * | 9/2010 | Leveillard et al. ........... 530/350 |
| 8,114,849 | B2 * | 2/2012 | Leveillard et al. ......... 514/44 R |
| 2009/0011040 | A1 * | 1/2009 | Naash et al. .................. 424/501 |

FOREIGN PATENT DOCUMENTS

| | | | |
|---|---|---|---|
| WO | 01/53312 | 7/2001 | |
| WO | 02/081513 | 10/2002 | |
| WO | WO02/081513 | * 10/2002 | ............. C07K 14/47 |
| WO | 2005/113586 | 12/2005 | |
| WO | WO2005/113586 | * 12/2005 | ............. C07K 14/47 |

OTHER PUBLICATIONS

Leveillard et al. Nature Genetics, 2004; 36:755-759.*
Chalmel et al. BMC Mol. Biol. 2007; 8: 74-86.*
Tang et al., "Novel nucleic acids and polypeptides, useful for treating disorders such as central nervous system injuries," Database Geneseq, Jul. 26, 2001, XP002499025.
International Search Report in PCT/EP08/57031, dated Nov. 5, 2008.

* cited by examiner

*Primary Examiner* — Chang-Yu Wang
(74) *Attorney, Agent, or Firm* — Whitham, Curtis & Cook, P.C.

(57) ABSTRACT

The present disclosure concerns a pharmaceutical composition comprising a pharmaceutically acceptable carrier and a compound selected in the group comprising (i) a polypeptide comprising an amino acid sequence selected in the group comprising the amino acid sequence of the long isoform in *Homo sapiens* of the RdCVF2 gene (SEQ ID NO:10), orthologs, derivatives and fragments thereof, (ii) a polynucleotide coding for said polypeptide, (iii) a vector comprising said polynucleotide, and (iv) a host cell genetically engineered expressing said polypeptide; the use of such a composition for the manufacture of a medicament for treating and/or preventing a neurodegenerative disorder in a subject; and a method of testing a subject thought to have or be predisposed to having a neurodegenerative disorder.

1 Claim, 7 Drawing Sheets

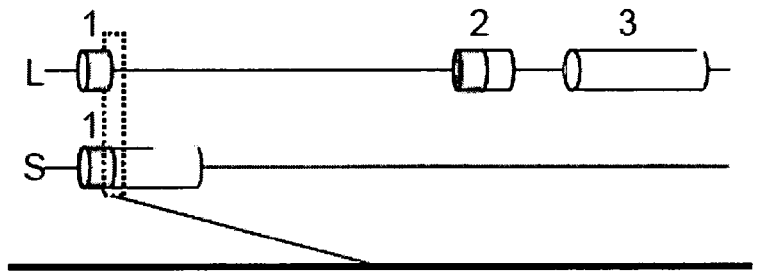

a   RdCVF gene, chromosome 8 minus strand

| | RdCVF-L | E..L..R..▼ |
|---|---|---|
| | RdCVF-S | E..L..R..R..*.. |
| *M. musculus* | | GAACTGAGGAGGTGAGGCCCC |
| *R. norvegicus* | | GACCTGAGGAGGTGAGGCCCC |
| *M. domestica* | | GAGCTGAAAAGGTGAGCCTAC |
| *H. sapiens* | | GATCTGAGGAGGTGAGGAGGG |
| *P. troglodytes* | | GATCTGAGGAGGTGAGGAGGG |
| *M. mulatta* | | GAACTGAGGAGGTGAsGGAGGG |
| *B. taurus* | | GACCTGAGGAGGTGAGACAAG |
| *C. familiaris* | | GACCTGAGGAGGTGAGGTGGG |
| *G. gallus* | | GACCTGAGGAGGTGG[n110]TAA |
| *X. tropicalis* | | GAATTCAGGAGGTGAGATAGG |
| *B. rerio* | | CCCTATAGGCAGTAC[n36]TGA |
| *T. rubripes a* | | CCATACAGACAGTAGGTGGAT |
| *T. nigroviridis a* | | CCATACAGACAGTAGGTGGAC |
| *T. rubripes b* | | CCCTTCAGGAGGTGTGTGGTTTAG |
| *T. nigroviridis b* | | CCTTTTAGGAGGTGT[n40]TGA |

| | L | S |
|---|---|---|
| 5'UTR | 22 bp | 44 bp |
| CDS | 654 bp | 330 bp |
| 3'UTR | 2076 bp | 798 bp |

Figure 1a

Cell viability (% of control)

SEQUENCE LISTING

```
<160> NUMBER OF SEQ ID NOS: 78

<210> SEQ ID NO 1
<211> LENGTH: 101
<212> TYPE: PRT
<213> ORGANISM: Homo sapiens

<400> SEQUENCE: 1

Met Val Asp Ile Leu Gly Glu Arg His Leu Val Thr Cys Lys Gly Ala
1               5                   10                  15

Thr Val Glu Ala Glu Ala Ala Leu Gln Asn Lys Val Val Ala Leu Tyr
            20                  25                  30

Phe Ala Ala Ala Arg Cys Ala Pro Ser Arg Asp Phe Thr Pro Leu Leu
        35                  40                  45

Cys Asp Phe Tyr Thr Ala Leu Val Ala Glu Ala Arg Arg Pro Ala Pro
    50                  55                  60

Phe Glu Val Val Phe Val Ser Ala Asp Gly Ser Ser Gln Glu Met Leu
65                  70                  75                  80

Asp Phe Met Arg Glu Leu His Gly Ala Trp Leu Ala Leu Pro Phe His
                85                  90                  95

Asp Pro Tyr Arg Gln
            100

<210> SEQ ID NO 2
<211> LENGTH: 101
<212> TYPE: PRT
<213> ORGANISM: Mus musculus

<400> SEQUENCE: 2

Met Val Asp Val Leu Gly Gly Arg Arg Leu Val Thr Arg Glu Gly Thr
1               5                   10                  15

Val Val Glu Ala Glu Val Ala Leu Gln Asn Lys Val Val Ala Leu Tyr
            20                  25                  30

Phe Ala Ala Gly Arg Cys Ser Pro Ser Arg Asp Phe Thr Pro Leu Leu
        35                  40                  45

Cys Asp Phe Tyr Thr Glu Leu Val Ser Glu Ala Arg Arg Pro Ala Pro
    50                  55                  60

Phe Glu Val Val Phe Val Ser Ala Asp Gly Ser Ala Glu Glu Met Leu
65                  70                  75                  80

Asp Phe Met Arg Glu Leu His Gly Ser Trp Leu Ala Leu Pro Phe His
                85                  90                  95

Asp Pro Tyr Arg Gln
            100

<210> SEQ ID NO 3
<211> LENGTH: 101
<212> TYPE: PRT
<213> ORGANISM: Rattus norvegicus

<400> SEQUENCE: 3
```

```
Met Val Asp Val Leu Gly Gly Arg Arg Leu Met Thr Arg Glu Gly Thr
1               5                   10                  15

Leu Val Glu Ala Glu Ala Ala Leu Gln Asn Lys Val Val Ala Leu Tyr
            20                  25                  30

Phe Ala Ala Gly Arg Cys Ala Pro Ser Arg Asp Phe Thr Pro Leu Leu
            35                  40                  45

Cys Asp Phe Tyr Thr Glu Leu Val Ser Glu Ala Arg Arg Pro Ala Pro
50                  55                  60

Phe Glu Val Val Phe Val Ser Ala Asp Arg Ser Ala Glu Glu Met Leu
65                  70                  75                  80

Asp Phe Met Arg Glu Leu His Gly Ser Trp Leu Ala Leu Pro Phe His
                85                  90                  95

Asp Pro Tyr Arg Gln
                100

<210> SEQ ID NO 4
<211> LENGTH: 101
<212> TYPE: PRT
<213> ORGANISM: Pan troglodytes

<400> SEQUENCE: 4

Met Val Asp Ile Leu Gly Gly Arg His Leu Val Thr Cys Lys Gly Ala
1               5                   10                  15

Thr Val Glu Ala Glu Ala Ala Leu Gln Asn Lys Val Val Ala Leu Tyr
            20                  25                  30

Phe Ala Ala Ala Arg Cys Ala Pro Ser Arg Asp Phe Thr Pro Leu Leu
            35                  40                  45

Cys Asp Phe Tyr Thr Ala Leu Val Ala Glu Ala Arg Arg Pro Ala Pro
50                  55                  60

Phe Glu Val Val Phe Val Ser Ala Asp Gly Ser Ser Gln Glu Met Leu
65                  70                  75                  80

Asp Phe Met Arg Glu Leu His Gly Ala Trp Leu Ala Leu Pro Phe His
                85                  90                  95

Asp Pro Tyr Arg Gln
                100

<210> SEQ ID NO 5
<211> LENGTH: 101
<212> TYPE: PRT
<213> ORGANISM: Bos taurus

<400> SEQUENCE: 5

Met Val Asp Val Leu Gly Gly Arg Arg Leu Val Thr Cys Asp Gly Ala
1               5                   10                  15

Trp Val Glu Ala Glu Ala Ala Leu Gln Asn Lys Val Val Ala Leu Tyr
            20                  25                  30

Phe Ala Ala Gly Arg Cys Ala Pro Ser Arg Asp Phe Thr Pro Leu Leu
            35                  40                  45

Cys Asp Phe Tyr Glu Glu Leu Val Asp Asp Ala Arg Pro Pro Ala Pro
50                  55                  60

Phe Glu Val Val Phe Val Ser Ala Asp Gly Ser Ala His Glu Met Leu
65                  70                  75                  80

Glu Phe Met Lys Glu Leu His Gly Ala Trp Leu Ala Leu Pro Phe His
                85                  90                  95

Asp Pro Tyr Arg Gln
                100
```

```
<210> SEQ ID NO 6
<211> LENGTH: 101
<212> TYPE: PRT
<213> ORGANISM: Gallus gallus

<400> SEQUENCE: 6

Met Val Asp Val Phe Ser Gly Arg Leu Leu Val Ser Lys Asp Gly Arg
1               5                   10                  15

Ser Val Asp Pro Glu Glu Ala Leu Gln Asn Lys Val Gly Gly Leu Tyr
                20                  25                  30

Phe Ser Ala Gly Trp Cys Ser Pro Cys Arg Asp Phe Thr Pro Val Leu
            35                  40                  45

Cys Asp Phe Tyr Thr Asp Leu Leu Glu Glu Cys Gln Pro Pro Ala Pro
50                  55                  60

Phe Glu Val Val Phe Ile Ser Ser Asp His Ser Ala Glu Glu Met Val
65                  70                  75                  80

Ser Tyr Met His Ser Met His Gly Asp Trp Leu Ala Leu Pro Phe His
                85                  90                  95

Asp Pro Tyr Lys Gln
            100

<210> SEQ ID NO 7
<211> LENGTH: 100
<212> TYPE: PRT
<213> ORGANISM: Xenopus laevis

<400> SEQUENCE: 7

Met Asp Ile Phe Ser Gly His Ile Leu Leu Asn Lys Tyr Gly Glu Arg
1               5                   10                  15

Val Asp Pro Glu Glu Ala Leu Gln Asn Lys Ile Val Gly Leu Tyr Phe
                20                  25                  30

Ser Ala Ser Trp Cys Ser Pro Cys Arg Asp Phe Thr Pro Ile Leu Cys
            35                  40                  45

Asp Phe Tyr Thr Glu Leu Val Glu Glu Ser Glu Pro Pro Ala Gln Phe
50                  55                  60

Glu Ile Val Phe Ile Ser Ser Asp Lys Ser Pro Glu Glu Met Val Asp
65                  70                  75                  80

Tyr Met His Asp Met Gln Gly Asp Trp Leu Ala Leu Pro Phe His Asp
                85                  90                  95

Pro Tyr Lys Gln
            100

<210> SEQ ID NO 8
<211> LENGTH: 101
<212> TYPE: PRT
<213> ORGANISM: Tetraodon nigroviridis

<400> SEQUENCE: 8

Met Val Glu Val Phe Thr Gly Arg Thr Leu Leu Asn Lys Asp Gly Asp
1               5                   10                  15

Leu Val Asp Pro Glu Glu Ala Leu Arg Asn Lys Val Val Gly Ile Tyr
                20                  25                  30

Phe Ser Ala Gly Trp Cys Pro Pro Cys Arg Asp Phe Thr Pro Ile Leu
            35                  40                  45

Cys Asp Phe Tyr Thr Glu Leu Val Glu Glu Ser Asp Pro Pro Ala Gln
50                  55                  60
```

```
Phe Glu Val Val Phe Val Ser Ser Asp Lys Thr Ser Glu Asp Met Val
 65                  70                  75                  80

Glu Tyr Tyr His Asp Leu His Gly Asp Trp Leu Ala Leu Pro Trp Ser
                 85                  90                  95

Asp Asp Tyr Lys Lys
            100

<210> SEQ ID NO 9
<211> LENGTH: 101
<212> TYPE: PRT
<213> ORGANISM: Danio rerio

<400> SEQUENCE: 9

Met Val Glu Val Phe Ser Gly Arg Thr Leu Val Asn Lys Glu Gly Asp
 1               5                  10                  15

Leu Val Glu Pro Glu Ala Leu Arg Asn Lys Val Val Gly Leu Tyr
             20                  25                  30

Phe Ser Ala Gly Trp Cys Pro Pro Cys Arg Asp Phe Thr Pro Leu Leu
             35                  40                  45

Cys Asp Phe Tyr Thr Glu Leu Val Glu Thr Glu Pro Pro Ala Gln
 50                  55                  60

Phe Glu Ile Val Phe Ile Ser Ser Asp Lys Ser Thr Glu Asp Met Val
 65                  70                  75                  80

Glu Tyr Tyr His Asp Met His Gly Asp Trp Leu Ala Leu Pro Trp Thr
                 85                  90                  95

Asp Pro Tyr Lys Gln
            100

<210> SEQ ID NO 10
<211> LENGTH: 156
<212> TYPE: PRT
<213> ORGANISM: Homo sapiens

<400> SEQUENCE: 10

Met Val Asp Ile Leu Gly Glu Arg His Leu Val Thr Cys Lys Gly Ala
 1               5                  10                  15

Thr Val Glu Ala Glu Ala Ala Leu Gln Asn Lys Val Val Ala Leu Tyr
             20                  25                  30

Phe Ala Ala Ala Arg Cys Ala Pro Ser Arg Asp Phe Thr Pro Leu Leu
             35                  40                  45

Cys Asp Phe Tyr Thr Ala Leu Val Ala Glu Ala Arg Arg Pro Ala Pro
 50                  55                  60

Phe Glu Val Val Phe Val Ser Ala Asp Gly Ser Ser Gln Glu Met Leu
 65                  70                  75                  80

Asp Phe Met Arg Glu Leu His Gly Ala Trp Leu Ala Leu Pro Phe His
                 85                  90                  95

Asp Pro Tyr Arg His Glu Leu Arg Lys Arg Tyr Asn Val Thr Ala Ile
            100                 105                 110

Pro Lys Leu Val Ile Val Lys Gln Asn Gly Glu Val Ile Thr Asn Lys
            115                 120                 125

Gly Arg Lys Gln Ile Arg Glu Arg Gly Leu Ala Cys Phe Gln Asp Trp
        130                 135                 140

Val Glu Ala Ala Asp Ile Phe Gln Asn Phe Ser Val
145                 150                 155

<210> SEQ ID NO 11
<211> LENGTH: 306
```

<212> TYPE: DNA
<213> ORGANISM: Homo sapiens

<400> SEQUENCE: 11

```
atggttgaca ttctgggcga gcggcacctg gtgacctgta agggcgcgac ggtggaggcc     60
gaggcggcgc tgcagaacaa ggtggtggca ctgtacttcg cggcggcccg gtgcgcgccg    120
agccgcgact tcacgccgct gctctgcgac ttctatacgg cgctggtggc cgaggcgcgg    180
cggcccgcgc ccttcgaagt ggtcttcgtg tcagccgacg gcagctccca ggagatgctg    240
gacttcatgc gcgagctgca tggcgcctgg ctggcgctgc ccttccacga ccctaccgg     300
cagtga                                                               306
```

<210> SEQ ID NO 12
<211> LENGTH: 156
<212> TYPE: PRT
<213> ORGANISM: Mus musculus

<400> SEQUENCE: 12

```
Met Val Asp Val Leu Gly Gly Arg Arg Leu Val Thr Arg Glu Gly Thr
1               5                   10                  15
Val Val Glu Ala Glu Val Ala Leu Gln Asn Lys Val Val Ala Leu Tyr
            20                  25                  30
Phe Ala Ala Gly Arg Cys Ser Pro Ser Arg Asp Phe Thr Pro Leu Leu
        35                  40                  45
Cys Asp Phe Tyr Thr Glu Leu Val Ser Glu Ala Arg Arg Pro Ala Pro
    50                  55                  60
Phe Glu Val Val Phe Val Ser Ala Asp Gly Ser Ala Glu Glu Met Leu
65                  70                  75                  80
Asp Phe Met Arg Glu Leu His Gly Ser Trp Leu Ala Leu Pro Phe His
                85                  90                  95
Asp Pro Tyr Arg His Glu Leu Lys Lys Arg Tyr Glu Ile Thr Ala Ile
            100                 105                 110
Pro Lys Leu Val Val Ile Lys Gln Asn Gly Ala Val Ile Thr Asn Lys
        115                 120                 125
Gly Arg Lys Gln Ile Arg Glu Arg Gly Leu Ala Cys Phe Gln Asn Trp
    130                 135                 140
Val Glu Ala Ala Asp Val Phe Gln Asn Phe Ser Gly
145                 150                 155
```

<210> SEQ ID NO 13
<211> LENGTH: 22
<212> TYPE: DNA
<213> ORGANISM: Artificial sequence
<220> FEATURE:
<223> OTHER INFORMATION: Synthetic-Primer

<400> SEQUENCE: 13

```
catcaccaac aaagggcgga ag                                              22
```

<210> SEQ ID NO 14
<211> LENGTH: 23
<212> TYPE: DNA
<213> ORGANISM: Artificial sequence
<220> FEATURE:
<223> OTHER INFORMATION: Synthetic-Primer

<400> SEQUENCE: 14

```
cattcctcag cagagaaggg aac                                             23
```

<210> SEQ ID NO 15
<211> LENGTH: 35
<212> TYPE: DNA
<213> ORGANISM: Artificial sequence
<220> FEATURE:
<223> OTHER INFORMATION: Synthetic-Primer

<400> SEQUENCE: 15
ccgtgctatt gtttcagagc ccttaacttt ctatc                              35

<210> SEQ ID NO 16
<211> LENGTH: 31
<212> TYPE: DNA
<213> ORGANISM: Artificial sequence
<220> FEATURE:
<223> OTHER INFORMATION: Synthetic-Primer

<400> SEQUENCE: 16
tgacactcca atcgtaaaag gcagaaaacg c                                  31

<210> SEQ ID NO 17
<211> LENGTH: 19
<212> TYPE: DNA
<213> ORGANISM: Artificial sequence
<220> FEATURE:
<223> OTHER INFORMATION: Synthetic-Primer

<400> SEQUENCE: 17
aagccgatga gcaacttcc                                                19

<210> SEQ ID NO 18
<211> LENGTH: 20
<212> TYPE: DNA
<213> ORGANISM: Artificial sequence
<220> FEATURE:
<223> OTHER INFORMATION: Synthetic-Primer

<400> SEQUENCE: 18
tcatctccca gtggattctt                                               20

<210> SEQ ID NO 19
<211> LENGTH: 21
<212> TYPE: DNA
<213> ORGANISM: Artificial sequence
<220> FEATURE:
<223> OTHER INFORMATION: Synthetic-Primer

<400> SEQUENCE: 19
gtagctttgt actttgcggc g                                             21

<210> SEQ ID NO 20
<211> LENGTH: 29
<212> TYPE: DNA
<213> ORGANISM: Artificial sequence
<220> FEATURE:
<223> OTHER INFORMATION: Synthetic-Primer

<400> SEQUENCE: 20
gtcatcagaa aatgtatcac ctccatagg                                     29

<210> SEQ ID NO 21
<211> LENGTH: 25
<212> TYPE: DNA
<213> ORGANISM: Artificial sequence
<220> FEATURE:
<223> OTHER INFORMATION: Synthetic-Primer

```
<400> SEQUENCE: 21
gccatctctg cgacttattt ttacc                                              25

<210> SEQ ID NO 22
<211> LENGTH: 22
<212> TYPE: DNA
<213> ORGANISM: Artificial sequence
<220> FEATURE:
<223> OTHER INFORMATION: Synthetic-Primer

<400> SEQUENCE: 22
aattagtgcc accagcacca tc                                                 22

<210> SEQ ID NO 23
<211> LENGTH: 4
<212> TYPE: PRT
<213> ORGANISM: Artificial sequence
<220> FEATURE:
<223> OTHER INFORMATION: Synthetic - Figure 1 - RdCVF-S

<400> SEQUENCE: 23

Glu Leu Arg Arg
1

<210> SEQ ID NO 24
<211> LENGTH: 21
<212> TYPE: DNA
<213> ORGANISM: Artificial sequence
<220> FEATURE:
<223> OTHER INFORMATION: Synthetic - Figure 1 - RdCVF-S - M. musculus

<400> SEQUENCE: 24
gaactgagga ggtgaggccc c                                                  21

<210> SEQ ID NO 25
<211> LENGTH: 21
<212> TYPE: DNA
<213> ORGANISM: Artificial sequence
<220> FEATURE:
<223> OTHER INFORMATION: Synthetic - Figure 1 - RdCVF-S - R. norvegicus

<400> SEQUENCE: 25
gacctgagga ggtgaggccc c                                                  21

<210> SEQ ID NO 26
<211> LENGTH: 21
<212> TYPE: DNA
<213> ORGANISM: Artificial sequence
<220> FEATURE:
<223> OTHER INFORMATION: Synthetic - Figure 1 - RdCVF-S - M. domestica

<400> SEQUENCE: 26
gagctgaaaa ggtgagccta c                                                  21

<210> SEQ ID NO 27
<211> LENGTH: 21
<212> TYPE: DNA
<213> ORGANISM: Artificial sequence
<220> FEATURE:
<223> OTHER INFORMATION: Synthetic - Figure 1 - RdCVF-S - H. sapiens

<400> SEQUENCE: 27
gatctgagga ggtgaggagg g                                                  21
```

```
<210> SEQ ID NO 28
<211> LENGTH: 21
<212> TYPE: DNA
<213> ORGANISM: Artificial sequence
<220> FEATURE:
<223> OTHER INFORMATION: Synthetic - Figure 1 - RdCVF-S - P. troglodytes

<400> SEQUENCE: 28
gatctgagga ggtgaggagg g                                             21

<210> SEQ ID NO 29
<211> LENGTH: 22
<212> TYPE: DNA
<213> ORGANISM: Artificial sequence
<220> FEATURE:
<223> OTHER INFORMATION: Figure 1 - RdCVF-S - M. mulatta

<400> SEQUENCE: 29
gaactgagga ggtgasggag gg                                            22

<210> SEQ ID NO 30
<211> LENGTH: 21
<212> TYPE: DNA
<213> ORGANISM: Artificial sequence
<220> FEATURE:
<223> OTHER INFORMATION: Synthetic - Figure 1 - RdCVF-S - B. taurus

<400> SEQUENCE: 30
gacctgagga ggtgagacaa g                                             21

<210> SEQ ID NO 31
<211> LENGTH: 21
<212> TYPE: DNA
<213> ORGANISM: Artificial sequence
<220> FEATURE:
<223> OTHER INFORMATION: Synthetic - Figure 1 - RdCVF-S - C. familiaris

<400> SEQUENCE: 31
gacctgagga ggtgaggtgg g                                             21

<210> SEQ ID NO 32
<211> LENGTH: 128
<212> TYPE: DNA
<213> ORGANISM: Artificial sequence
<220> FEATURE:
<223> OTHER INFORMATION: Figure 1 - RdCVF-S - G. gallus
<220> FEATURE:
<221> NAME/KEY: misc_feature
<222> LOCATION: (16)..(115)
<223> OTHER INFORMATION: N= A, T, G or C
<220> FEATURE:
<221> NAME/KEY: misc_feature
<222> LOCATION: (116)..(125)
<223> OTHER INFORMATION: n is a, c, g, or t

<400> SEQUENCE: 32
gacctgagga ggtggnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120 nnnnntaa                                                            128

<210> SEQ ID NO 33
<211> LENGTH: 21
<212> TYPE: DNA
<213> ORGANISM: Artificial sequence
<220> FEATURE:
<223> OTHER INFORMATION: Synthetic - Figure 1 - RdCVF-S -X. tropicalis
```

-continued

<400> SEQUENCE: 33
gaattcagga ggtgagatag g        21

<210> SEQ ID NO 34
<211> LENGTH: 54
<212> TYPE: DNA
<213> ORGANISM: Artificial sequence
<220> FEATURE:
<223> OTHER INFORMATION: Synthetic - Figure 1 - RdCVF-S -B. rerio
<220> FEATURE:
<221> NAME/KEY: misc_feature
<222> LOCATION: (16)..(51)
<223> OTHER INFORMATION: N= A, T, G or C

<400> SEQUENCE: 34
ccctataggc agtacnnnnn nnnnnnnnnn nnnnnnnnnn nnnnnnnnnn ntga        54

<210> SEQ ID NO 35
<211> LENGTH: 21
<212> TYPE: DNA
<213> ORGANISM: Artificial sequence
<220> FEATURE:
<223> OTHER INFORMATION: Synthetic - Figure 1 - RdCVF-S -T. rubripes

<400> SEQUENCE: 35
ccatacagac agtaggtgga t        21

<210> SEQ ID NO 36
<211> LENGTH: 21
<212> TYPE: DNA
<213> ORGANISM: Artificial sequence
<220> FEATURE:
<223> OTHER INFORMATION: Synthetic - Figure 1 - RdCVF-S -T. nigroviridis

<400> SEQUENCE: 36
ccatacagac agtaggtgga c        21

<210> SEQ ID NO 37
<211> LENGTH: 24
<212> TYPE: DNA
<213> ORGANISM: Artificial sequence
<220> FEATURE:
<223> OTHER INFORMATION: Synthetic - Figure 1 - RdCVF-S -T. rubripes

<400> SEQUENCE: 37
cccttcagga ggtgtgtggt ttag        24

<210> SEQ ID NO 38
<211> LENGTH: 58
<212> TYPE: DNA
<213> ORGANISM: Artificial sequence
<220> FEATURE:
<223> OTHER INFORMATION: Figure 1 - RdCVF-S - T. nigroviridis
<220> FEATURE:
<221> NAME/KEY: misc_feature
<222> LOCATION: (16)..(55)
<223> OTHER INFORMATION: N= A, T, G or C

<400> SEQUENCE: 38
ccttttagga ggtgtnnnnn nnnnnnnnnn nnnnnnnnnn nnnnnnnnnn nnnnntga        58

<210> SEQ ID NO 39
<211> LENGTH: 4
<212> TYPE: PRT
<213> ORGANISM: Artificial sequence
<220> FEATURE:
<223> OTHER INFORMATION: Synthetic - Figure 1- RdCVF2-L

```
<400> SEQUENCE: 39

Pro Tyr Arg His
1

<210> SEQ ID NO 40
<211> LENGTH: 4
<212> TYPE: PRT
<213> ORGANISM: Artificial sequence
<220> FEATURE:
<223> OTHER INFORMATION: Synthetic - Figure 1- RdCVF2-S

<400> SEQUENCE: 40

Pro Tyr Arg Gln
1

<210> SEQ ID NO 41
<211> LENGTH: 23
<212> TYPE: DNA
<213> ORGANISM: Artificial sequence
<220> FEATURE:
<223> OTHER INFORMATION: Synthetic - Figure 1 - RdCVF2-S - M. musculus

<400> SEQUENCE: 41
ccctaccggc agtgagtggg gac                                          23

<210> SEQ ID NO 42
<211> LENGTH: 23
<212> TYPE: DNA
<213> ORGANISM: Artificial sequence
<220> FEATURE:
<223> OTHER INFORMATION: Synthetic - Figure 1 - RdCVF2-S - R. norvegicus

<400> SEQUENCE: 42
ccctaccggc agtgagtggg gac                                          23

<210> SEQ ID NO 43

<400> SEQUENCE: 43

000

<210> SEQ ID NO 44
<211> LENGTH: 23
<212> TYPE: DNA
<213> ORGANISM: Artificial sequence
<220> FEATURE:
<223> OTHER INFORMATION: Synthetic - Figure 1 - RdCVF2-S - H. sapiens

<400> SEQUENCE: 44
ccctaccggc agtgagtggg ggc                                          23

<210> SEQ ID NO 45
<211> LENGTH: 23
<212> TYPE: DNA
<213> ORGANISM: Artificial sequence
<220> FEATURE:
<223> OTHER INFORMATION: Synthetic - Figure 1 - RdCVF2-S -
     P. troglodytes

<400> SEQUENCE: 45
ccctaccggc agtgagtggg ggc                                          23

<210> SEQ ID NO 46
<211> LENGTH: 23
<212> TYPE: DNA
```

```
<213> ORGANISM: Artificial sequence
<220> FEATURE:
<223> OTHER INFORMATION: Synthetic - Figure 1 - RdCVF2-S - M. mulatta

<400> SEQUENCE: 46
ccctaccagc agtgagtggg ggc                                               23

<210> SEQ ID NO 47
<211> LENGTH: 23
<212> TYPE: DNA
<213> ORGANISM: Artificial sequence
<220> FEATURE:
<223> OTHER INFORMATION: Synthetic - Figure 1 - RdCVF2-S - B. taurus

<400> SEQUENCE: 47
ccctaccggc agtgagtgga ggc                                               23

<210> SEQ ID NO 48
<211> LENGTH: 23
<212> TYPE: DNA
<213> ORGANISM: Artificial sequence
<220> FEATURE:
<223> OTHER INFORMATION: Synthetic - Figure 1 - RdCVF2-S - G. gallus

<400> SEQUENCE: 48
ccctacaagc agtaagtacc gca                                               23

<210> SEQ ID NO 49
<211> LENGTH: 23
<212> TYPE: DNA
<213> ORGANISM: Artificial sequence
<220> FEATURE:
<223> OTHER INFORMATION: Synthetic - Figure 1 - RdCVF2-S -X. tropicalis

<400> SEQUENCE: 49
ccatacaagc agtaagttcc ttg                                               23

<210> SEQ ID NO 50
<211> LENGTH: 23
<212> TYPE: DNA
<213> ORGANISM: Artificial sequence
<220> FEATURE:
<223> OTHER INFORMATION: Synthetic - Figure 1 - RdCVF2-S -B. rerio

<400> SEQUENCE: 50
ccatacaaac agtgagttca cca                                               23

<210> SEQ ID NO 51
<211> LENGTH: 23
<212> TYPE: DNA
<213> ORGANISM: Artificial sequence
<220> FEATURE:
<223> OTHER INFORMATION: Synthetic - Figure 1 - RdCVF2-S -T. rubripes

<400> SEQUENCE: 51
gactacaaga agtgagtgag gtt                                               23

<210> SEQ ID NO 52
<211> LENGTH: 23
<212> TYPE: DNA
<213> ORGANISM: Artificial sequence
<220> FEATURE:
<223> OTHER INFORMATION: Synthetic - Figure 1 - RdCVF2-S -T.
      nigroviridis

<400> SEQUENCE: 52
```
gactacaaga agtgagtccg cct                                           23

<210> SEQ ID NO 53
<211> LENGTH: 109
<212> TYPE: PRT
<213> ORGANISM: Escherichia coli

<400> SEQUENCE: 53

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 54
<211> LENGTH: 105
<212> TYPE: PRT
<213> ORGANISM: Homo sapiens

<400> SEQUENCE: 54

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 55
<211> LENGTH: 435
<212> TYPE: PRT
<213> ORGANISM: Mus musculus

<400> SEQUENCE: 55

Met Ser Gly Phe Leu Glu Glu Leu Leu Gly Asp Lys Leu Val Thr Gly
1               5                   10                  15

Gly Gly Glu Glu Val Asp Val His Ser Leu Gly Ala Arg Gly Ile Ala
            20                  25                  30

Leu Leu Gly Leu Tyr Phe Gly Cys Ser Leu Ser Ala Pro Cys Ala Gln
        35                  40                  45

Leu Ser Ala Ser Leu Ala Ala Phe Tyr Gly Arg Leu Arg Gly Asp Ala
    50                  55                  60

-continued

```
Ala Ala Gly Pro Gly Ala Gly Ala Gly Ala Ala Glu Pro
 65                  70                  75                  80

Glu Pro Arg His Arg Leu Glu Ile Val Phe Val Ser Asp Gln Asp
                 85                  90                  95

Gln Arg Gln Trp Gln Asp Phe Val Arg Asp Met Pro Trp Leu Ala Leu
            100                 105                 110

Pro Tyr Lys Glu Lys His Arg Lys Leu Lys Leu Trp Asn Lys Tyr Arg
            115                 120                 125

Val Ser Asn Ile Pro Ser Leu Ile Phe Leu Asp Ala Thr Thr Gly Lys
130                 135                 140

Val Val Cys Arg Asn Gly Leu Leu Val Ile Arg Asp Asp Pro Glu Gly
145                 150                 155                 160

Leu Glu Phe Pro Trp Gly Pro Lys Pro Phe Arg Glu Val Ile Ala Gly
                165                 170                 175

Pro Leu Leu Arg Asn Asn Gly Gln Ser Leu Glu Ser Ser Ser Leu Glu
                180                 185                 190

Gly Ser His Val Gly Val Tyr Phe Ser Ala His Trp Cys Pro Pro Cys
                195                 200                 205

Arg Ser Leu Thr Arg Val Leu Val Glu Ser Tyr Arg Lys Ile Lys Glu
210                 215                 220

Ala Gly Gln Glu Phe Glu Ile Ile Phe Val Ser Ala Asp Arg Ser Glu
225                 230                 235                 240

Glu Ser Phe Lys Gln Tyr Phe Ser Glu Met Pro Trp Leu Ala Val Pro
                245                 250                 255

Tyr Thr Asp Glu Ala Arg Arg Ser Arg Leu Asn Arg Leu Tyr Gly Ile
                260                 265                 270

Gln Gly Ile Pro Thr Leu Ile Val Leu Asp Pro Gln Gly Glu Val Ile
                275                 280                 285

Thr Arg Gln Gly Arg Val Glu Val Leu Asn Asp Glu Asp Cys Arg Glu
290                 295                 300

Phe Pro Trp His Pro Lys Pro Val Leu Glu Leu Ser Asp Ser Asn Ala
305                 310                 315                 320

Val Gln Leu Asn Glu Gly Pro Cys Leu Val Leu Phe Val Asp Ser Glu
                325                 330                 335

Asp Asp Gly Glu Ser Glu Ala Ala Lys Gln Leu Ile Gln Pro Ile Ala
                340                 345                 350

Glu Lys Ile Ile Ala Lys Tyr Lys Ala Lys Glu Glu Ala Pro Leu
            355                 360                 365

Leu Phe Phe Val Ala Gly Glu Asp Asp Met Thr Asp Ser Leu Arg Asp
            370                 375                 380

Tyr Thr Asn Leu Pro Glu Ala Ala Pro Leu Leu Thr Ile Leu Asp Met
385                 390                 395                 400

Ser Ala Arg Ala Lys Tyr Val Met Asp Val Glu Glu Ile Thr Pro Ala
                405                 410                 415

Ile Val Glu Thr Phe Val Asn Asp Phe Leu Ala Glu Lys Leu Lys Pro
                420                 425                 430

Glu Pro Ile
            435
```

<210> SEQ ID NO 56
<211> LENGTH: 146
<212> TYPE: PRT
<213> ORGANISM: Crithidia fasciculata

<400> SEQUENCE: 56

| Met | Ser | Gly | Leu | Asp | Lys | Tyr | Leu | Pro | Gly | Ile | Glu | Lys | Leu | Arg | Arg |
| 1 | | | | 5 | | | | | 10 | | | | | 15 | |

| Gly | Asp | Gly | Glu | Val | Glu | Val | Lys | Ser | Leu | Ala | Gly | Lys | Leu | Val | Phe |
| | | | 20 | | | | | 25 | | | | | 30 | | |

| Phe | Tyr | Phe | Ser | Ala | Ser | Trp | Cys | Pro | Pro | Cys | Arg | Gly | Phe | Thr | Pro |
| | | 35 | | | | | 40 | | | | | 45 | | | |

| Gln | Leu | Ile | Glu | Phe | Tyr | Asp | Lys | Phe | His | Glu | Ser | Lys | Asn | Phe | Glu |
| 50 | | | | | 55 | | | | | 60 | | | | | |

| Val | Val | Phe | Cys | Thr | Trp | Asp | Glu | Glu | Asp | Gly | Phe | Ala | Gly | Tyr |
| 65 | | | | 70 | | | | | 75 | | | | | 80 |

| Phe | Ala | Lys | Met | Pro | Trp | Leu | Ala | Val | Pro | Phe | Ala | Gln | Ser | Glu | Ala |
| | | | 85 | | | | | 90 | | | | | 95 | | |

| Val | Gln | Lys | Leu | Ser | Lys | His | Phe | Asn | Val | Glu | Ser | Ile | Pro | Thr | Leu |
| | | | 100 | | | | | 105 | | | | | 110 | | |

| Ile | Gly | Val | Asp | Ala | Asp | Ser | Gly | Asp | Val | Val | Thr | Thr | Arg | Ala | Arg |
| | | | 115 | | | | | 120 | | | | | 125 | | |

| Ala | Thr | Leu | Val | Lys | Asp | Pro | Glu | Gly | Glu | Gln | Phe | Pro | Trp | Lys | Asp |
| | 130 | | | | | 135 | | | | | 140 | | | | |

Ala Pro
145

<210> SEQ ID NO 57
<211> LENGTH: 156
<212> TYPE: PRT
<213> ORGANISM: Mus musculus

<400> SEQUENCE: 57

| Met | Val | Asp | Val | Leu | Gly | Gly | Arg | Arg | Leu | Val | Thr | Arg | Glu | Gly | Thr |
| 1 | | | | 5 | | | | | 10 | | | | | 15 | |

| Val | Val | Glu | Ala | Glu | Val | Ala | Leu | Gln | Asn | Lys | Val | Val | Ala | Leu | Tyr |
| | | | 20 | | | | | 25 | | | | | 30 | | |

| Phe | Ala | Ala | Gly | Arg | Cys | Ser | Pro | Ser | Arg | Asp | Phe | Thr | Pro | Leu | Leu |
| | | 35 | | | | | 40 | | | | | 45 | | | |

| Cys | Asp | Phe | Tyr | Thr | Glu | Leu | Val | Ser | Glu | Ala | Arg | Arg | Pro | Ala | Pro |
| 50 | | | | | 55 | | | | | 60 | | | | | |

| Phe | Glu | Val | Val | Phe | Val | Ser | Ala | Asp | Gly | Ser | Ala | Glu | Met | Leu |
| 65 | | | | 70 | | | | | 75 | | | | | 80 |

| Asp | Phe | Met | Arg | Glu | Leu | His | Gly | Ser | Trp | Leu | Ala | Leu | Pro | Phe | His |
| | | | 85 | | | | | 90 | | | | | 95 | | |

| Asp | Pro | Tyr | Arg | His | Glu | Leu | Lys | Lys | Arg | Tyr | Glu | Ile | Thr | Ala | Ile |
| | | | 100 | | | | | 105 | | | | | 110 | | |

| Pro | Lys | Leu | Val | Val | Ile | Lys | Gln | Asn | Gly | Ala | Val | Ile | Thr | Asn | Lys |
| | | | 115 | | | | | 120 | | | | | 125 | | |

| Gly | Arg | Lys | Gln | Ile | Arg | Glu | Arg | Gly | Leu | Ala | Cys | Phe | Gln | Asn | Trp |
| | 130 | | | | | 135 | | | | | 140 | | | | |

| Val | Glu | Ala | Ala | Asp | Val | Phe | Gln | Asn | Phe | Ser | Gly |
| 145 | | | | | 150 | | | | | 155 | |

<210> SEQ ID NO 58
<211> LENGTH: 101
<212> TYPE: PRT
<213> ORGANISM: Mus musculus

<400> SEQUENCE: 58

| Met | Val | Asp | Val | Leu | Gly | Gly | Arg | Arg | Leu | Val | Thr | Arg | Glu | Gly | Thr |

```
          1               5                  10                 15
Val Val Glu Ala Glu Val Ala Leu Gln Asn Lys Val Val Ala Leu Tyr
            20                  25                 30

Phe Ala Ala Gly Arg Cys Ser Pro Ser Arg Asp Phe Thr Pro Leu Leu
            35                  40                 45

Cys Asp Phe Tyr Thr Glu Leu Val Ser Glu Ala Arg Arg Pro Ala Pro
 50                      55                 60

Phe Glu Val Val Phe Val Ser Ala Asp Gly Ser Ala Glu Glu Met Leu
 65                      70                 75                 80

Asp Phe Met Arg Glu Leu His Gly Ser Trp Leu Ala Leu Pro Phe His
                 85                  90                 95

Asp Pro Tyr Arg Gln
                100

<210> SEQ ID NO 59
<211> LENGTH: 156
<212> TYPE: PRT
<213> ORGANISM: Rattus norvegicus

<400> SEQUENCE: 59

Met Val Asp Val Leu Gly Gly Arg Arg Leu Met Thr Arg Glu Gly Thr
 1               5                  10                 15

Leu Val Glu Ala Glu Ala Ala Leu Gln Asn Lys Val Val Ala Leu Tyr
            20                  25                 30

Phe Ala Ala Gly Arg Cys Ala Pro Ser Arg Asp Phe Thr Pro Leu Leu
            35                  40                 45

Cys Asp Phe Tyr Thr Glu Leu Val Ser Glu Ala Arg Arg Pro Ala Pro
 50                      55                 60

Phe Glu Val Val Phe Val Ser Ala Asp Arg Ser Ala Glu Glu Met Leu
 65                      70                 75                 80

Asp Phe Met Arg Glu Leu His Gly Ser Trp Leu Ala Leu Pro Phe His
                 85                  90                 95

Asp Pro Tyr Arg His Glu Leu Lys Lys Arg Tyr Asp Ile Thr Val Ile
                100                 105                110

Pro Lys Val Val Ile Lys Gln Asn Gly Ala Val Ile Thr Asn Lys
            115                 120                125

Gly Arg Lys Gln Ile Arg Glu Arg Gly Leu Ala Cys Phe Gln Asn Trp
            130                 135                140

Val Glu Ala Ala Asp Val Phe Gln Asn Phe Ser Gly
145                 150                 155

<210> SEQ ID NO 60
<211> LENGTH: 156
<212> TYPE: PRT
<213> ORGANISM: Homo sapiens

<400> SEQUENCE: 60

Met Val Asp Ile Leu Gly Glu Arg His Leu Val Thr Cys Lys Gly Ala
 1               5                  10                 15

Thr Val Glu Ala Glu Ala Ala Leu Gln Asn Lys Val Val Ala Leu Tyr
            20                  25                 30

Phe Ala Ala Ala Arg Cys Ala Pro Ser Arg Asp Phe Thr Pro Leu Leu
            35                  40                 45

Cys Asp Phe Tyr Thr Ala Leu Val Ala Glu Ala Arg Arg Pro Ala Pro
 50                      55                 60

Phe Glu Val Val Phe Val Ser Ala Asp Gly Ser Ser Gln Glu Met Leu
```

```
                65                  70                  75                  80
Asp Phe Met Arg Glu Leu His Gly Ala Trp Leu Ala Leu Pro Phe His
                    85                  90                  95
Asp Pro Tyr Arg His Glu Leu Arg Lys Arg Tyr Asn Val Thr Ala Ile
                100                 105                 110
Pro Lys Leu Val Ile Val Lys Gln Asn Gly Glu Val Ile Thr Asn Lys
            115                 120                 125
Gly Arg Lys Gln Ile Arg Glu Arg Gly Leu Ala Cys Phe Gln Asp Trp
        130                 135                 140
Val Glu Ala Ala Asp Ile Phe Gln Asn Phe Ser Val
145                 150                 155

<210> SEQ ID NO 61
<211> LENGTH: 156
<212> TYPE: PRT
<213> ORGANISM: Pan troglodytes

<400> SEQUENCE: 61

Met Val Asp Ile Leu Gly Gly Arg His Leu Val Thr Cys Lys Gly Ala
1               5                   10                  15
Thr Val Glu Ala Glu Ala Ala Leu Gln Asn Lys Val Val Ala Leu Tyr
                20                  25                  30
Phe Ala Ala Ala Arg Cys Ala Pro Ser Arg Asp Phe Thr Pro Leu Leu
            35                  40                  45
Cys Asp Phe Tyr Thr Ala Leu Val Ala Glu Ala Arg Arg Pro Ala Pro
        50                  55                  60
Phe Glu Val Val Phe Val Ser Ala Asp Gly Ser Gln Glu Met Leu
65                  70                  75                  80
Asp Phe Met Arg Glu Leu His Gly Ala Trp Leu Ala Leu Pro Phe His
                    85                  90                  95
Asp Pro Tyr Arg His Glu Leu Arg Lys Arg Tyr Asn Val Thr Ala Ile
                100                 105                 110
Pro Lys Leu Val Ile Val Lys Gln Asn Gly Glu Val Ile Thr Asn Lys
            115                 120                 125
Gly Arg Lys Gln Ile Arg Glu Arg Gly Leu Ala Cys Phe Gln Asp Trp
        130                 135                 140
Val Glu Ala Ala Asp Ile Phe Gln Asn Phe Ser Val
145                 150                 155

<210> SEQ ID NO 62
<211> LENGTH: 156
<212> TYPE: PRT
<213> ORGANISM: Bos taurus

<400> SEQUENCE: 62

Met Val Asp Val Leu Gly Gly Arg Arg Leu Val Thr Cys Asp Gly Ala
1               5                   10                  15
Trp Val Glu Ala Glu Ala Ala Leu Gln Asn Lys Val Val Ala Leu Tyr
                20                  25                  30
Phe Ala Ala Gly Arg Cys Ala Pro Ser Arg Asp Phe Thr Pro Leu Leu
            35                  40                  45
Cys Asp Phe Tyr Glu Glu Leu Val Asp Asp Ala Arg Pro Pro Ala Pro
        50                  55                  60
Phe Glu Val Val Phe Val Ser Ala Asp Gly Ser Ala His Glu Met Leu
65                  70                  75                  80
Glu Phe Met Lys Glu Leu His Gly Ala Trp Leu Ala Leu Pro Phe His
```

```
                    85                  90                  95

Asp Pro Tyr Arg His Glu Leu Arg Thr Arg Tyr His Ile Thr Ala Ile
                100                 105                 110

Pro Arg Leu Val Ile Leu Lys Pro Ser Gly Glu Val Ile Thr Asp Lys
            115                 120                 125

Gly Arg Lys Gln Ile Arg Glu Arg Gly Leu Ala Cys Phe Gln Asn Trp
130                 135                 140

Val Glu Ala Ala Asp Ile Phe Gln Asn Phe Ser Ser
145                 150                 155

<210> SEQ ID NO 63
<211> LENGTH: 156
<212> TYPE: PRT
<213> ORGANISM: Gallus gallus

<400> SEQUENCE: 63

Met Val Asp Val Phe Ser Gly Arg Leu Leu Val Ser Lys Asp Gly Arg
1               5                   10                  15

Ser Val Asp Pro Glu Glu Ala Leu Gln Asn Lys Val Gly Gly Leu Tyr
                20                  25                  30

Phe Ser Ala Gly Trp Cys Ser Pro Cys Arg Asp Phe Thr Pro Val Leu
            35                  40                  45

Cys Asp Phe Tyr Thr Asp Leu Leu Glu Glu Cys Gln Pro Pro Ala Pro
        50                  55                  60

Phe Glu Val Val Phe Ile Ser Ser Asp His Ser Ala Glu Glu Met Val
65                  70                  75                  80

Ser Tyr Met His Ser Met His Gly Asp Trp Leu Ala Leu Pro Phe His
                85                  90                  95

Asp Pro Tyr Lys His Asp Leu Lys Lys Lys Tyr Asn Ile Thr Ala Ile
                100                 105                 110

Pro Lys Leu Val Ile Val Lys Gln Thr Gly Glu Val Ile Thr Asp Lys
            115                 120                 125

Gly Arg Lys Gln Ile Arg Asp Lys Gly Leu Ser Cys Phe Arg Asn Trp
130                 135                 140

Leu Glu Gly Ala Asp Ile Phe Gln Asn Phe Ser Ser
145                 150                 155

<210> SEQ ID NO 64
<211> LENGTH: 156
<212> TYPE: PRT
<213> ORGANISM: Xenopus laevis

<400> SEQUENCE: 64

Met Asp Ile Phe Ser Gly His Ile Leu Leu Asn Lys Tyr Gly Glu Arg
1               5                   10                  15

Val Asp Pro Glu Glu Ala Leu Gln Asn Lys Ile Val Gly Leu Tyr Phe
                20                  25                  30

Ser Ala Ser Trp Cys Ser Pro Cys Arg Asp Phe Thr Pro Ile Leu Cys
            35                  40                  45

Asp Phe Tyr Thr Glu Leu Val Glu Ser Glu Pro Pro Ala Gln Phe
        50                  55                  60

Glu Ile Val Phe Ile Ser Ser Asp Lys Ser Pro Glu Glu Met Val Asp
65                  70                  75                  80

Tyr Met His Asp Met Gln Gly Asp Trp Leu Ala Leu Pro Phe His Asp
                85                  90                  95

Pro Tyr Lys His Glu Leu Lys Asn Lys Tyr Lys Ile Thr Ala Ile Pro
```

```
                    100                 105                 110
Lys Leu Val Ile Val Lys Gln Asn Gly Asp Val Ile Thr Asp Lys Gly
                115                 120                 125

Arg Lys Gln Ile Arg Glu Arg Gly Leu Ser Cys Phe Arg Thr Trp Leu
            130                 135                 140

Glu Val Gly Asp Val Phe Gln Asn Phe Thr Gly Lys
145                 150                 155

<210> SEQ ID NO 65
<211> LENGTH: 156
<212> TYPE: PRT
<213> ORGANISM: Tetraodon nigroviridis

<400> SEQUENCE: 65

Met Val Glu Val Phe Thr Gly Arg Thr Leu Leu Asn Lys Asp Gly Asp
1               5                   10                  15

Leu Val Asp Pro Glu Glu Ala Leu Arg Asn Lys Val Val Gly Ile Tyr
                20                  25                  30

Phe Ser Ala Gly Trp Cys Pro Pro Cys Arg Asp Phe Thr Pro Ile Leu
            35                  40                  45

Cys Asp Phe Tyr Thr Glu Leu Val Glu Glu Ser Asp Pro Pro Ala Gln
        50                  55                  60

Phe Glu Val Val Phe Val Ser Ser Asp Lys Thr Ser Glu Asp Met Val
65                  70                  75                  80

Glu Tyr Tyr His Asp Leu His Gly Asp Trp Leu Ala Leu Pro Trp Ser
                85                  90                  95

Asp Asp Tyr Lys Asn Glu Leu Lys Gln Arg Tyr Lys Ile Thr Ala Val
                100                 105                 110

Pro Lys Leu Val Ile Val Lys Glu Ser Gly Glu Val Ile Thr Asp Lys
                115                 120                 125

Gly Arg Lys Gln Ile Arg Asp Arg Gly Leu Ala Cys Phe Arg Ser Trp
            130                 135                 140

Leu Asp Ala Ala Glu Val Phe Gln Asn Phe Glu Gly
145                 150                 155

<210> SEQ ID NO 66
<211> LENGTH: 156
<212> TYPE: PRT
<213> ORGANISM: Danio rerio

<400> SEQUENCE: 66

Met Val Glu Val Phe Ser Gly Arg Thr Leu Val Asn Lys Glu Gly Asp
1               5                   10                  15

Leu Val Glu Pro Glu Glu Ala Leu Arg Asn Lys Val Val Gly Leu Tyr
                20                  25                  30

Phe Ser Ala Gly Trp Cys Pro Pro Cys Arg Asp Phe Thr Pro Leu Leu
            35                  40                  45

Cys Asp Phe Tyr Thr Glu Leu Val Glu Glu Thr Glu Pro Pro Ala Gln
        50                  55                  60

Phe Glu Ile Val Phe Ile Ser Ser Asp Lys Ser Thr Glu Asp Met Val
65                  70                  75                  80

Glu Tyr Tyr His Asp Met His Gly Asp Trp Leu Ala Leu Pro Trp Thr
                85                  90                  95

Asp Pro Tyr Lys His Glu Leu Lys Lys Arg Tyr Asn Ile Thr Ala Val
                100                 105                 110

Pro Lys Leu Val Ile Val Lys Glu Asn Gly Gln Val Ile Thr Asp Lys
```

```
                     115                 120                 125
Gly Arg Lys Gln Ile Arg Asp Gln Gly Leu Ala Cys Phe Arg Ser Trp
    130                 135                 140

Ile Glu Val Ala Glu Ile Phe Gln Asn Phe Lys Gly
145                 150                 155

<210> SEQ ID NO 67
<211> LENGTH: 217
<212> TYPE: PRT
<213> ORGANISM: Mus musculus

<400> SEQUENCE: 67

Met Ala Ser Leu Phe Ser Gly Arg Ile Leu Ile Arg Asn Asn Ser Asp
1               5                  10                  15

Gln Asp Glu Val Glu Thr Glu Ala Glu Leu Ser Arg Arg Leu Glu Asn
                20                  25                  30

Arg Leu Val Leu Leu Phe Phe Gly Ala Gly Ala Cys Pro Gln Cys Gln
            35                  40                  45

Ala Phe Ala Pro Val Leu Lys Asp Phe Phe Val Arg Leu Thr Asp Glu
        50                  55                  60

Phe Tyr Val Leu Arg Ala Ala Gln Leu Ala Leu Val Tyr Val Ser Gln
65                  70                  75                  80

Asp Pro Thr Glu Glu Gln Gln Asp Leu Phe Leu Arg Asp Met Pro Glu
                85                  90                  95

Lys Trp Leu Phe Leu Pro Phe His Asp Glu Leu Arg Arg Asp Leu Gly
            100                 105                 110

Arg Gln Phe Ser Val Arg Gln Leu Pro Ala Val Val Leu Lys Pro
        115                 120                 125

Gly Gly Asp Val Leu Thr Ser Asp Ala Thr Glu Glu Ile Gln Arg Leu
    130                 135                 140

Gly Pro Ala Cys Phe Ala Asn Trp Gln Glu Ala Ala Glu Leu Leu Asp
145                 150                 155                 160

Arg Ser Phe Leu Gln Pro Glu Asp Leu Asp Glu Pro Ala Arg Arg Ser
                165                 170                 175

Ile Thr Glu Pro Leu Arg Arg Lys Tyr Arg Val Asp Arg Asp Val
            180                 185                 190

Gly Arg Glu Arg Gly Arg Asn Gly Arg Asp Ser Gly Asp Pro Gln Gly
        195                 200                 205

Asp Ala Gly Thr Arg Ala Glu Leu Trp
    210                 215

<210> SEQ ID NO 68
<211> LENGTH: 109
<212> TYPE: PRT
<213> ORGANISM: Mus musculus

<400> SEQUENCE: 68

Met Ala Ser Leu Phe Ser Gly Arg Ile Leu Ile Arg Asn Asn Ser Asp
1               5                  10                  15

Gln Asp Glu Val Glu Thr Glu Ala Glu Leu Ser Arg Arg Leu Glu Asn
                20                  25                  30

Arg Leu Val Leu Leu Phe Phe Gly Ala Gly Ala Cys Pro Gln Cys Gln
            35                  40                  45

Ala Phe Ala Pro Val Leu Lys Asp Phe Phe Val Arg Leu Thr Asp Glu
        50                  55                  60

Phe Tyr Val Leu Arg Ala Ala Gln Leu Ala Leu Val Tyr Val Ser Gln
```

```
                65                  70                  75                  80
Asp Pro Thr Glu Glu Gln Gln Asp Leu Phe Leu Arg Asp Met Pro Glu
                    85                  90                  95

Lys Trp Leu Phe Leu Pro Phe His Asp Glu Leu Arg Arg
                100                 105
```

<210> SEQ ID NO 69
<211> LENGTH: 576
<212> TYPE: PRT
<213> ORGANISM: Rattus norvegicus

<400> SEQUENCE: 69

```
Met Val Ser Leu Phe Ser Gly Arg Ile Leu Ile Arg Asn Asn Ser Asp
1               5                   10                  15

Gln Asp Glu Val Glu Thr Glu Ala Glu Leu Ser Arg Arg Leu Glu Asn
                20                  25                  30

Arg Leu Val Leu Leu Phe Phe Gly Ala Gly Ala Cys Pro Gln Cys Gln
                35                  40                  45

Ala Phe Ala Pro Val Leu Lys Asp Phe Phe Val Arg Leu Thr Asp Glu
            50                  55                  60

Phe Tyr Val Leu Arg Ala Ala Gln Leu Ala Leu Val Tyr Val Ser Gln
65                  70                  75                  80

Asp Pro Thr Glu Glu Gln Gln Asp Leu Phe Leu Arg Asp Met Pro Glu
                85                  90                  95

Lys Trp Leu Phe Leu Pro Phe His Asp Asp Leu Arg Arg Asp Leu Gly
                100                 105                 110

Arg Gln Phe Ser Val Arg Gln Leu Pro Ala Val Val Leu Lys Pro
                115                 120                 125

Gly Gly Asp Val Leu Thr Ser Asp Ala Thr Asp Glu Ile Gln Arg Leu
            130                 135                 140

Gly Pro Ala Cys Phe Ala Asn Trp Gln Glu Ala Ala Glu Leu Leu Asp
145                 150                 155                 160

Arg Ser Phe Leu Gln Pro Glu Asp Leu Asp Glu Pro Ala Arg Arg Ser
                165                 170                 175

Ile Thr Glu Pro Leu Arg Arg Arg Lys Tyr Arg Val Asp Arg Asp Ala
                180                 185                 190

Gly Arg Gly Arg Gly Arg Asn Glu Cys Asp Ser Arg Asn Pro Gln Gly
            195                 200                 205

Gly Arg Gly Cys Arg Asp Gly Ala Leu Val Ile Pro Pro Ala Pro Gln
        210                 215                 220

Gly Thr Arg Val His Trp Trp Asn Phe Gly Asp Leu Gln Gly Asn Ser
225                 230                 235                 240

Gly Leu Gly Ile Gly Val Gln Leu Arg Val Gln Pro Val Gly Ala Tyr
                245                 250                 255

Ala Pro Gln Leu Arg Ala Pro Cys Leu Glu Leu Gln Gln Leu Arg
                260                 265                 270

Ser Gln Arg Asp Gln His Arg Gly Arg Asp Ala Gln Lys Gly His Arg
            275                 280                 285

Gly Gln Tyr Pro Ala Ser Ala Cys Ala Met Gly Arg Ser Tyr Gly Gly
        290                 295                 300

Arg Val Leu Ala Ala Met Thr Leu Leu Gly Ile Pro Ala Ala Val Leu
305                 310                 315                 320

Val Ala Leu Ala Ala Gln Leu Leu Phe Gln Leu Gln Ala Gly Arg Ala
                325                 330                 335
```

-continued

Glu Leu Arg Gly Ile Arg Thr Asp Gly Leu His Pro Glu Leu Asp Pro
                340                 345                 350

Asp Ala Gly Leu Pro Glu Ala Ala Gly Ala Leu Leu Pro Leu Ala
            355                 360                 365

Thr Ala Leu Ala Ala Leu Ala Gln Val Leu Gly Leu Gly Cys Leu Leu
    370                 375                 380

Leu Ala Ala Leu Cys Gly His Leu Gly Ala Glu Leu Ala Arg Gly Pro
385                 390                 395                 400

Gly Pro Gly Arg Leu Thr Leu Asn Val Trp Ser Cys Phe Asn Leu Pro
                405                 410                 415

Asn Leu Gly Arg Arg Ala Leu Ala Ile Tyr Ala Leu Leu Phe Glu
            420                 425                 430

Ile Glu Ala Gly Ala Ala Ala Ser Ile Leu Gly Ser Gly Ala Leu
            435                 440                 445

Ile Leu Val Ala Ile Met Thr His Thr Leu Phe Arg Ala Val Gln Ala
    450                 455                 460

Thr Arg Arg Gly Leu Arg Glu Leu Pro Pro Ser Ser Glu Asp Glu
465                 470                 475                 480

Pro Ala Arg Ser Ser Glu Asp Ser Lys Ala Gly Cys Arg Ala Gln Pro
                485                 490                 495

Gln Gln Gly Thr His Cys Gln Ile Phe Tyr Asn Pro Ser Gln Glu Leu
            500                 505                 510

Gly Asp Pro Pro Gly Ser Met Ala Thr Cys Ile Thr Ser Ala Val Leu
            515                 520                 525

Glu Arg Ala Ser Glu Ser Ser Leu Leu Ala Ser His Leu Pro Gln Thr
    530                 535                 540

Leu Arg Ser Met Gly Pro Trp Asp Gly Val Thr Tyr Glu Met His Gly
545                 550                 555                 560

Met Leu Gly His Arg Pro Pro Asp Met Gly Lys Asp Ala Thr Leu Val
                565                 570                 575

<210> SEQ ID NO 70
<211> LENGTH: 212
<212> TYPE: PRT
<213> ORGANISM: Homo sapiens

<400> SEQUENCE: 70

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Leu Phe Phe Gly Ala Gly Ala Cys Pro Gln Cys Gln
        35                  40                  45

Ala Phe Val Pro Ile Leu Lys Asp Phe Val Arg Leu Thr Asp Glu
    50                  55                  60

Phe Tyr Val Leu Arg Ala Ala Gln Leu Ala Leu Val Tyr Val Ser Gln
65                  70                  75                  80

Asp Ser Thr Glu Glu Gln Gln Asp Leu Phe Leu Lys Asp Met Pro Lys
            85                  90                  95

Lys Trp Leu Phe Leu Pro Phe Glu Asp Asp Leu Arg Arg Asp Leu Gly
                100                 105                 110

Arg Gln Phe Ser Val Glu Arg Leu Pro Ala Val Val Leu Lys Pro
            115                 120                 125

Asp Gly Asp Val Leu Thr Arg Asp Gly Ala Asp Glu Ile Gln Arg Leu
    130                 135                 140

Gly Thr Ala Cys Phe Ala Asn Trp Gln Glu Ala Ala Glu Val Leu Asp
145                 150                 155                 160

Arg Asn Phe Gln Leu Pro Glu Asp Leu Glu Asp Gln Glu Pro Arg Ser
            165                 170                 175

Leu Thr Glu Cys Leu Arg Arg His Lys Tyr Arg Val Gly Lys Ala Ala
            180                 185                 190

Arg Gly Gly Arg Asp Pro Gly Gly Gly Gly Glu Glu Gly Gly Ala
        195                 200                 205

Gly Gly Leu Phe
    210

<210> SEQ ID NO 71
<211> LENGTH: 202
<212> TYPE: PRT
<213> ORGANISM: Pan troglodytes
<220> FEATURE:
<221> NAME/KEY: misc_feature
<222> LOCATION: (168)..(201)
<223> OTHER INFORMATION: Xaa can be any naturally occurring amino acid

<400> SEQUENCE: 71

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Leu Phe Phe Gly Ala Gly Ala Cys Pro Gln Cys Gln
        35                  40                  45

Ala Phe Val Pro Ile Leu Lys Asp Phe Val Arg Leu Thr Asp Glu
50                  55                  60

Phe Tyr Val Leu Arg Ala Ala Gln Leu Ala Leu Val Tyr Val Ser Gln
65                  70                  75                  80

Asp Ser Thr Glu Glu Gln Gln Asp Leu Phe Leu Lys Asp Met Pro Lys
                85                  90                  95

Lys Trp Leu Phe Leu Pro Phe Glu Asp Asp Leu Arg Arg Asp Leu Gly
            100                 105                 110

Arg Gln Phe Ser Val Glu Arg Leu Pro Ala Val Val Leu Lys Pro
        115                 120                 125

Asp Gly Asp Val Leu Thr Arg Asp Gly Ala Asp Glu Ile Gln Arg Leu
130                 135                 140

Gly Thr Ala Cys Phe Ala Asn Trp Gln Glu Ala Ala Glu Val Leu Asp
145                 150                 155                 160

Arg Asn Phe Gln Leu Pro Glu Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Ala
        195                 200

<210> SEQ ID NO 72
<211> LENGTH: 218
<212> TYPE: PRT
<213> ORGANISM: Canis familiaris

<400> SEQUENCE: 72

Met Ala Ser Leu Phe Ser Gly Arg Val Leu Ile Arg Asn Asn Ser Asp
1               5                   10                  15

Gln Asp Glu Leu Asp Thr Glu Ala Glu Leu Ser Arg Arg Leu Glu Asn

```
            20                  25                  30
Arg Leu Val Leu Leu Phe Phe Gly Ala Gly Ser Cys Pro Gln Cys Gln
            35                  40                  45

Ala Phe Ala Pro Ile Leu Arg Asp Phe Phe Val Arg Leu Thr Asp Glu
        50                  55                  60

Phe Tyr Val Leu Arg Ala Ala Gln Leu Ala Leu Val Tyr Val Ser Gln
65                  70                  75                  80

Asp Pro Thr Glu Glu Gln Gln Asp Leu Phe Leu Arg Asp Met Pro Lys
                85                  90                  95

Lys Trp Leu Phe Leu Pro Phe Glu Asp Leu Arg Arg Asp Leu Gly
            100                 105                 110

Arg Arg Phe Ser Val Glu Arg Leu Pro Ala Val Val Leu Lys Pro
        115                 120                 125

Gly Gly Asp Val Leu Ser Arg Asp Ala Thr Asp Glu Ile Arg Arg Leu
130                 135                 140

Gly Pro Ala Cys Phe Ala Asn Trp Gln Glu Ala Ala Glu Val Leu Asp
145                 150                 155                 160

Arg Asn Phe Leu Gln Pro Glu Asp Leu Asp Asp Pro Ala Pro Arg Ser
                165                 170                 175

Leu Thr Glu Pro Leu Arg Arg Cys Lys Tyr Arg Val Asp Arg Glu Ala
            180                 185                 190

Arg Gly Lys Arg Gly Pro Gly Gly Ser Gln Pro Glu Gly Gly Arg
        195                 200                 205

Gly Ala Glu Gly Gly Ala Gly Asp Leu Phe
210                 215

<210> SEQ ID NO 73
<211> LENGTH: 218
<212> TYPE: PRT
<213> ORGANISM: Bos taurus

<400> SEQUENCE: 73

Met Ala Ser Leu Phe Ser Gly Arg Val Leu Ile Arg Asn Asn Ser Asp
1               5                   10                  15

Gln Asp Glu Leu Asp Thr Glu Ala Glu Leu Ser Arg Arg Leu Glu Asn
            20                  25                  30

Arg Leu Val Leu Leu Phe Phe Gly Ala Gly Ser Cys Pro Glu Cys Gln
            35                  40                  45

Ala Phe Ala Pro Ile Leu Arg Asp Phe Phe Val Arg Leu Thr Asp Glu
        50                  55                  60

Phe Tyr Val Leu Arg Ala Ala Gln Val Ala Leu Val Tyr Val Ser Gln
65                  70                  75                  80

Asp Pro Thr Glu Glu Gln Gln Asp Leu Phe Leu Arg Asp Met Pro Glu
                85                  90                  95

Lys Trp Leu Phe Leu Pro Phe Glu Asp Asp Leu Arg Arg Asp Leu Gly
            100                 105                 110

Arg Gln Phe Ser Val Glu Arg Leu Pro Ala Val Val Leu Lys Pro
        115                 120                 125

Ser Gly Asp Val Leu Thr Leu Asp Ala Ala Asp Glu Ile Arg Arg Leu
130                 135                 140

Gly Pro Ala Cys Phe Ala Asn Trp Gln Glu Ala Ala Glu Val Leu Asp
145                 150                 155                 160

Arg Ser Phe Leu Gln Pro Glu Asp Leu Asp Asp Pro Ala Pro Arg Ser
                165                 170                 175
```

-continued

```
Leu Thr Glu Pro Leu Arg Arg Cys Lys Tyr Arg Val Asp Pro Ala Ala
            180                 185                 190

Arg Arg Ala Arg Gly Arg Gly Ala Gly Ser Gly Gln Glu Gly
        195                 200                 205

Glu Ala Glu Gly Glu Ala Ala Gly Leu Phe
    210                 215

<210> SEQ ID NO 74
<211> LENGTH: 207
<212> TYPE: PRT
<213> ORGANISM: Gallus gallus

<400> SEQUENCE: 74

Met Ala Ser Leu Phe Ala Gly Lys Val Leu Ile Val Asn Asn Arg Asp
1               5                   10                  15

Arg Asp Glu Val Glu Thr Glu Arg Glu Arg Cys Ser Ala Leu Glu Asn
                20                  25                  30

Arg Val Met Leu Leu Tyr Phe Gly Ala Ala Glu Cys Pro Arg Cys Gln
            35                  40                  45

Ser Phe Ala Pro Arg Leu Lys Asp Phe Phe Val Arg Leu Thr Asp Glu
    50                  55                  60

Phe Tyr Val Glu Arg Ala Ser Gln Leu Cys Leu Val Tyr Val Ser Arg
65                  70                  75                  80

Asp Ala Thr Ala Gln Gln Glu Glu Ala Phe Leu Arg Ser Met Pro Arg
                85                  90                  95

Arg Trp Leu Ser Leu Pro Phe Arg Asp Glu Phe Lys Arg Glu Leu Glu
            100                 105                 110

Leu Arg Phe Val Val Ser Glu Val Pro Arg Val Val Leu Lys Pro
    115                 120                 125

Asn Gly Asp Val Ile Val Gly Asn Ala Val Asp Glu Ile Thr Ser Met
130                 135                 140

Gly Pro Ala Cys Phe Gln Asn Trp Gln Glu Ala Ala Glu Leu Val Asp
145                 150                 155                 160

Arg Asn Phe Arg Leu Ala Glu Asp Phe Asp Glu Cys Ala Arg Arg Ser
                165                 170                 175

Ile Thr Asp Pro Leu Arg Arg Leu Lys Tyr Lys Leu Gly Lys Gly Glu
            180                 185                 190

Glu Pro Arg Ser Glu Gln Lys Glu Asp Gly Asp Glu Ser Ser
        195                 200                 205

<210> SEQ ID NO 75
<211> LENGTH: 215
<212> TYPE: PRT
<213> ORGANISM: Xenopus laevis

<400> SEQUENCE: 75

Met Ala Asp Leu Phe Leu Asp Lys Ile Leu Val Lys Asn Asn Arg Asp
1               5                   10                  15

Gln Asp Glu Leu Asp Thr Glu Arg Glu Ile Trp Glu Arg Leu Glu Asn
                20                  25                  30

Arg Val Ile Leu Leu Phe Phe Ala Lys Ser Arg Ser Ser Gln Cys Gln
            35                  40                  45

Glu Phe Ala Pro Leu Leu Lys Asp Phe Phe Val Arg Leu Thr Asp Glu
    50                  55                  60

Phe Tyr Val Asp Arg Ser Ser Gln Leu Ala Leu Val Tyr Val Ser Leu
65                  70                  75                  80
```

```
Asp Gln Ser Glu Glu Gln Glu Arg Phe Leu Lys Asp Met Pro Lys
            85                  90                  95

Arg Trp Leu Phe Val Pro Phe Lys Asp Glu Glu Phe Arg Asn Leu
            100                 105                 110

Glu Ala Gln Phe Ser Val Ser Arg Val Pro Val Leu Val Leu Lys
            115                 120                 125

Pro Ser Gly His Val Ile Ser Phe Asn Ala Val Asp Glu Val Val Arg
            130                 135                 140

Leu Gly Pro Pro Cys Phe Lys Asn Trp Gln Glu Val Ser Glu Ile Ile
145                 150                 155                 160

Asp Arg Ser Phe Leu Leu Pro Glu Phe Thr Asp Asp Arg Ala Gly Arg
                    165                 170                 175

Ser Met Thr Asp Pro Ile Arg Arg Ile Lys Tyr Lys Asp Glu Thr Thr
                180                 185                 190

Asn Glu Lys Lys Lys Arg Lys His Cys Asp Asp Glu Asp Gly Gly
            195                 200                 205

Gly Gly Gly Thr Glu Phe Phe
210                 215

<210> SEQ ID NO 76
<211> LENGTH: 180
<212> TYPE: PRT
<213> ORGANISM: Tetraodon nigroviridis

<400> SEQUENCE: 76

Met Val Asp Leu Phe Leu Asn Arg Val Leu Val Glu Asn Asn Trp Asp
1               5                   10                  15

Gln Asp Gln Leu Asn Thr Glu Arg Glu Ile Val Gly Ile Leu Glu Asn
            20                  25                  30

Arg Ile Leu Leu Leu Phe Ala Ser Ala Ser Cys Gln Lys Cys Gln
            35                  40                  45

Asp Phe Leu Pro Ile Leu Asn Asn Phe Phe Lys Arg Leu Lys Asp Pro
50                  55                  60

Ala His Ile Glu Tyr Pro Lys Leu Leu Ala Leu Ile Phe Ile Ser Leu
65                  70                  75                  80

Asp Gln Ser Glu Glu Gln Glu Arg Phe Leu Lys Glu Leu His Lys
            85                  90                  95

Lys Val Leu Phe Leu Ala Phe Asp Asp Pro Tyr Arg Gln Glu Leu Gln
            100                 105                 110

Ala Met Phe Glu Val Lys Glu Leu Pro Thr Val Val Leu Arg Pro
            115                 120                 125

Asp Gly Ser Val Leu Ala Ala Asn Ala Gln Asp Ile Cys Ser Tyr
            130                 135                 140

Gly Ser Glu Cys Phe Arg Asp Trp Gln Glu Ser Ala Glu Leu Ile Glu
145                 150                 155                 160

Arg Thr Phe Met Leu Asn Glu Glu Phe Asp Asn Leu Asn Leu Arg Thr
                    165                 170                 175

Ser Ala Thr Pro
            180

<210> SEQ ID NO 77
<211> LENGTH: 169
<212> TYPE: PRT
<213> ORGANISM: Tetraodon nigroviridis

<400> SEQUENCE: 77
```

Met Val Asp Leu Phe Ile Asp Arg Val Leu Leu Lys Asn Asn Ser Glu
1               5                   10                  15

Arg Asp Glu Leu Asp Thr Glu Arg Glu Ile Val Ala Arg Leu Gln Asn
            20                  25                  30

Arg Ile Leu Leu Leu Phe Phe Gly Cys Val Val Ser Arg Ser Cys Gln
        35                  40                  45

Leu Phe Ala Pro Lys Leu Ser Ser Phe Phe Lys Gln Leu Thr Asp Glu
    50                  55                  60

Ala Tyr Val Asp Arg Ser Ala Gln Leu Val Leu Leu Tyr Ile Ser Met
65                  70                  75                  80

Asp Gln Ser Glu Gln Gln Leu Ser Ser Phe Leu Gln Glu Leu Pro Lys
                85                  90                  95

Lys Cys Leu Phe Leu Ala Phe Glu Asp Pro Phe Arg Arg Glu Leu Glu
            100                 105                 110

Ala Met Phe Asn Val Glu Glu Leu Pro Thr Val Val Leu Arg Pro
        115                 120                 125

Asp Cys Ser Val Leu Ala Ala Asn Ala Val Glu Glu Ile Leu Arg Leu
    130                 135                 140

Gly Pro Asp Cys Tyr Arg Asn Trp Gln Glu Ala Ala Glu Leu Tyr Arg
145                 150                 155                 160

Gln Glu Leu Pro Asp Gln Arg Arg Leu
                165

<210> SEQ ID NO 78
<211> LENGTH: 215
<212> TYPE: PRT
<213> ORGANISM: Danio rerio

<400> SEQUENCE: 78

Met Val Asp Leu Phe Leu Gly Lys Val Leu Val Lys Asn Asn Lys Asp
1               5                   10                  15

Arg Asp Glu Leu Asp Thr Glu Arg Glu Ile Ile Leu Arg Leu Gln Asn
            20                  25                  30

Arg Ile Leu Met Leu Phe Phe Gly Ser Gly Asp Ser Glu Lys Cys Gln
        35                  40                  45

Asp Phe Ala Pro Thr Leu Lys Asp Phe Tyr Lys Leu Thr Asp Glu
    50                  55                  60

Phe Tyr Val Glu Arg Ser Ala Gln Leu Val Leu Leu Tyr Ile Ser Leu
65                  70                  75                  80

Asp Ser Ser Glu Glu Gln Gln Glu Lys Phe Leu Lys Glu Leu Pro Lys
                85                  90                  95

Arg Cys Leu Phe Leu Pro Tyr Glu Asp Pro Tyr Arg Gln Glu Leu Gly
            100                 105                 110

Val Met Phe Glu Val Arg Asp Leu Pro Arg Val Val Leu Arg Pro
        115                 120                 125

Asp Cys Ser Val Leu Ser Pro Asn Ala Val Ser Glu Ile Cys Thr Leu
    130                 135                 140

Gly Thr Asp Cys Phe Arg Asn Trp Gln Glu Gly Ala Glu Leu Ile Asp
145                 150                 155                 160

Arg Asn Phe Met Met Asn Glu Glu Phe Asp Glu Gly Lys Met Arg Ser
                165                 170                 175

Met Thr Asp Pro Ile Arg Arg Ile Lys Tyr Lys Val Glu Asp Glu Lys
            180                 185                 190

```
Lys Lys Lys Lys Lys Arg Asp Asp Asp Asp Asp Asp Gly Gly
        195                 200             205

Gly Gly Gly Gly Pro Trp Gly
    210             215
```

METHODS FOR TREATING CONE DYSTROPHY WITH NEURONAL VIABILITY FACTOR, RDCVF2

CROSS-REFERENCE TO RELATED APPLICATIONS

This application is a National Phase Entry of International Application No. PCT/EP2008/057031, filed on Jun. 5, 2008, which claims the priority of the patent application EP07109652.3 filed on Jun. 5, 2007, both of which are incorporated herein by reference.

FIELD OF THE INVENTION

The present invention relates to neurodegenerative disorders, and more particularly to a pharmaceutical composition for treating and/or preventing neurodegenerative disorders.

BACKGROUND OF THE INVENTION

Neurodegenerative disorders have provided a challenge for many years, in both basic research and clinical contexts. As an example of such a neurodegenerative disorder, retinitis pigmentosa (RP) is a genetically heterogeneous retinal degeneration characterized by the sequential degeneration of a population of neurons corresponding to rod and cone photoreceptors. The RP first clinical signs are night blindness and narrowing of the peripheral field of vision which progressively worsens to become "tunnel-like". Eventually, the central vision is reduced to complete blindness in most cases. At a cellular level, the retinal rod photoreceptors involved in night and side visions slowly degenerate. Subsequently, the cone photoreceptors responsible for both color and high-contrast vision, visual acuity, detail perception and normal light vision are similarly affected. The retinal degeneration 1 (rd1) mouse is the most studied animal model for retinitis pigmentosa. It carries a recessive mutation in the rod-specific cGMP phosphodiesterase beta subunit gene leading to rod photoreceptor death through apoptosis (CARTER-DAWSON et al., *Invest. Opthalmol. Vis. Sci.*, vol. 17(6), p: 489-498, 1978; PORTERA-CAILLIAU et al., *Proc. Natl. Acad. Sci. U.S.A*, vol. 91(3), p: 974-978, 1994) followed by cone death presumably through lack of trophic support (MOHAND-SAID et al., *Proc. Natl. Acad. Sci. U.S.A*, vol. 95(14), p: 8357-8362, 1998). Accordingly, the technical problem underlying the present invention is to provide novel compounds having neurotrophic activities, which compounds are suitable for the treatment of neurodegenerative disorders such as retinitis pigmentosa for which no treatment is actually available.

The RdCVF gene, also called thioredoxin-like 6 (Txn16) or Nucleoredoxin-like 1 (Nxnl1), encodes the Q8VC33 UniProt [6] protein, which has limited similarity to the thioredoxin superfamily and which exerts trophic activity on cone photoreceptors (LEVEILLARD et al., *Nat. Genet.* vol. 36(7), p: 755-759, 2004). Thioredoxins (TXN) are usually small proteins which can be involved with pleiotropic activities such as redox control, regulation of apoptosis and cytokine activity (HOLMGREN, *Annu. Rev. Biochem.*, vol. 54, p: 237-271, 1985; HOLMGREN, *J. Biol. Chem.*, vol. 264(24), p: 13963-13966, 1989; ARNER and HOLMGREN, *Eur. J. Biochem.*, vol. 267(20), p: 6102-6109, 2000). The TXN conserved active site contains two distinct cysteines (CXXC) that contribute to a thiol-oxydoreductase activity (ARNER and HOLMGREN, 2000, above-mentioned; POWIS and MONTFORT, *Annu. Rev. Pharmacol. Toxicol.*, vol. 41, p: 261-295, 2001) catalyzes the reduction of disulfide bonds in multiple substrate proteins (HOLMGREN, *J. Biol. Chem.*, vol. 254(18), p: 9113-9119, 1979; HOLMGREN, *J. Biol. Chem.*, vol. 254(19), p: 9627-9632, 1979). The RdCVF gene encodes two products via alternative splicing: a full length protein and a C-terminal post-transcriptionally truncated protein sharing similarities with TRX80. This latter form of human thioredoxin-1 (Txn) (PEKKARI et al., *J. Biol. Chem.*, vol. 275(48), p: 37474-37480, 2000; PEKKARI et al., *Blood*, vol. 105(4), p: 1598-1605, 2005; LIU et al., *Blood*, vol. 105(4), p: 1606-1613, 2005) has no thiol-reductase activity but is involved in controlling growth of peripheral mononuclear blood cells (PEKKARI et al., 2000, abovementioned; PEKKARI et al., *FEBS Lett.*, vol. 539(1-3), p: 143-148, 2003). Similar to Txn, RdCVF looks like a bifunctional gene because it encodes both a long form (RdCVF-L, 217 aa, Q8VC33) having a putative thiol-oxydoreductase activity (JEFFERY, *Trends Biochem. Sci.*, vol. 24(1), p: 8-11, 1999; JEFFERY, *Trends Genet.*, vol. 19(8), p: 415-417, 2003) and a short form (RdCVF-S, 109 aa, Q91 W38) with trophic activity for cones but no redox activity.

SUMMARY OF THE INVENTION

The present invention relates to a pharmaceutical composition comprising a pharmaceutically acceptable carrier and a compound selected in the group comprising:
  (i) a polypeptide comprising an amino acid sequence selected in the group comprising the amino acid sequence of the short isoform in *Homo sapiens* of the RdCVF2 gene (SEQ ID NO:1), orthologs, derivatives and fragments thereof;
  (ii) a polynucleotide coding for said polypeptide;
  (iii) a vector comprising said polynucleotide; and
  (iv) a host cell genetically engineered expressing said polypeptide.

In another embodiment, the present invention relates to a use, for treating and/or preventing a neurodegenerative disorder, of a compound selected in the group comprising:
  (i) a polypeptide comprising an amino acid sequence selected in the group comprising the amino acid sequence of the isoform in *Homo sapiens* of the RdCVF2 gene (SEQ ID NO:1), orthologs, derivatives and fragments thereof;
  (ii) a polynucleotide coding for said polypeptide;
  (iii) a vector comprising said polynucleotide; and
  (iv) a host cell genetically engineered expressing said polypeptide.

In still another embodiment, the present invention relates to a method of preventing and/or treating a neurodegenerative disease comprising providing, to a subject displaying or predicted to display a neurodegenerative disorder, an effective amount of a composition comprising a compound selected in the group comprising:
  (i) a polypeptide comprising an amino acid sequence selected in the group comprising the amino acid sequence of the short isoform in *Homo sapiens* of the RdCVF2 gene (SEQ ID NO:1), orthologs, derivatives and fragments thereof;
  (ii) a polynucleotide coding for said polypeptide;
  (iii) a vector comprising said polynucleotide; and
  (iv) a host cell genetically engineered expressing said polypeptide.

In still another embodiment, the present invention finally relates a method of testing a subject thought to have or be predisposed to having a neurodegenerative disorder, which comprises detecting the presence of a mutation in the RdCVF2 gene and/or its associated promoter in a biological sample from said subject

DETAILED DESCRIPTION

Figure 1B:
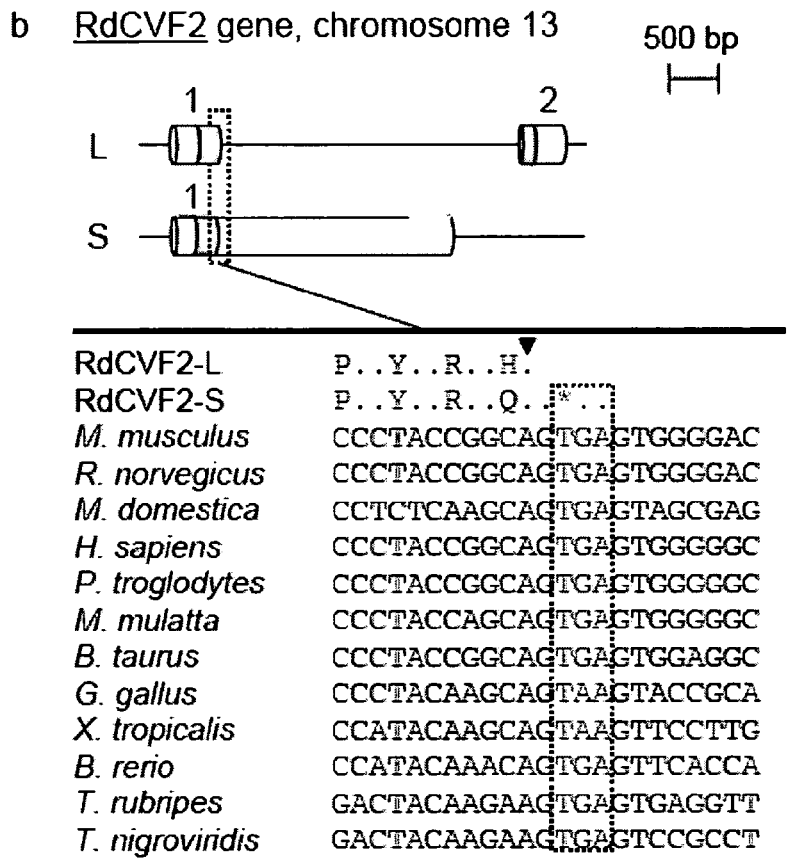
FIG. 1 shows the RdCVF and RdCVF2 gene structure conservation.

The present invention is based on the discovery of a new gene RdCVF2 as a gene paralogous to RdCVF, with the protein encoded by said gene enhancing the viability of neurons such as cone photoreceptors and olfactory neurons. Thus, in a first aspect, the present invention provides a pharmaceutical composition comprising a pharmaceutically acceptable carrier and a compound selected in the group comprising:

(i) a polypeptide comprising an amino acid sequence selected in the group comprising the amino acid sequence of the short isoform in *Homo sapiens* of the RdCVF2 gene (SEQ ID NO:1), orthologs, derivatives and fragments thereof;

(ii) a polynucleotide coding for said polypeptide;

(iii) a vector comprising said polynucleotide; and (iv) a host cell genetically engineered expressing said polypeptide.

As used herein, the term "polypeptide" refers to a molecular chain of amino acids enhancing the viability of neurons such as cone photoreceptors or olfactory neurons. This polypeptide, if required, can be modified in vitro and/or in vivo, for example by glycosylation, myristoylation, amidation, carboxylation or phosphorylation, and may be obtained, for example, by synthetic or recombinant techniques known in the art.

According to a preferred embodiment, the composition of the invention comprises a pharmaceutically acceptable carrier and a compound selected in the group comprising:

(i) a polypeptide comprising an amino acid sequence selected in the group comprising the amino acid sequence of the long isoform in *Homo sapiens* of the RdCVF2 gene (SEQ ID NO:10), orthologs, derivatives and fragments thereof;

(ii) a polynucleotide coding for said polypeptide;

(iii) a vector comprising said polynucleotide; and (iv) a host cell genetically engineered expressing said polypeptide.

As used herein, the term "orthologs" refers to proteins in different species than the proteins SEQ ID NO.1 and SEQ ID NO.10 in *Homo sapiens* that evolved from a common ancestral gene by speciation. As an example of such orthologs, one can cite the proteins corresponding to RdCVF2-S in *Mus musculus* (SEQ ID NO.2), *Rattus norvegicus* (SEQ ID NO.3), *Pan troglodytes* (SEQ ID NO.4), *Bos Taurus* (SEQ ID NO.5), *Gallus gallus* (SEQ ID NO.6), *Xenopus laevis* (SEQ ID NO.7), *Tetraodon nigroviridis* (SEQ ID NO.8), and *Danio rerio* (SEQ ID NO.9). As used herein, the term "derivatives" refers to polypeptides having a percentage of identity of at least 75% with SEQ ID NO.1, SEQ ID NO.10 or ortholog thereof, preferably of at least 85%, as an example of at least 90%, and more preferably of at least 95%. It has to be noted that the short isoform of RdCVF2 in *Homo sapiens* has less than 40% of identity with the short isoform of RdCVF in *Homo sapiens*. As used herein "fragments" refers to polypeptides having a length of at least 25 amino acids, preferably at least 50 amino acids, as an example at least 75 or 85 amino acids, and more preferably of at least 100 amino acids.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously align according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (*Ad. App. Math.*, vol. 2, p: 482, 1981), by using the local homology algorithm developed by NEDDLEMAN and WUNSCH (*J. Mol. Biol.*, vol. 48, p: 443, 1970), by using the method of similarities developed by PEARSON and LIPMAN (*Proc. Natl. Acd. Sci. USA*, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., *Nucleic Acids Research*, vol. 32, p: 1792, 2004). To get the best local alignment, one can preferably used BLAST software, with the BLOSUM 62 matrix, or the PAM 30 matrix. The identity percentage between two sequences of amino acids is determined by comparing these two sequences optimally aligned, the amino acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

As used herein, the term "polynucleotide" refers to RNA or DNA, preferably to DNA. Said DNA may be double-stranded or single-stranded. Preferably, the polynucleotide comprises the sequence SEQ ID NO.11. Preferably, the polynucleotide comprises a sequence which encodes the sequence SEQ ID NO:10. The polynucleotide of the invention may also include the coding sequence of the polypeptide defined previously, additional coding sequence such as leader sequence or a proprotein sequence, and/or additional non-coding sequence, such as introns or 5' and/or 3' UTR sequences.

As used herein, the term "vector" refers to an expression vector, and may be for example in the form of a plasmid, a viral particle, a phage, etc. Such vectors may include bacterial plasmids, phage DNA, baculovirus, yeast plasmids, vectors derived from combinations of plasmids and phage DNA, viral DNA such as vaccinia, adenovirus, fowl pox virus, and pseudorabies. Large numbers of suitable vectors are known to those of skill in the art and are commercially available. The following vectors are provided by way of example. Bacterial: pQE70, pQE60, pQE-9 (QIAGEN), pbs, pD10, phagescript, psiX174, pbluescript SK, pbsks, pNH8A, pNH16a, pNH18A, pNH46A (STRATAGENE), ptrc99a, pKK223-3, pKK233-3, pDR540, pRIT5 (PHARMACIA). Eukaryotic: pWLNEO, pSV2CAT, pOG44, pXT1, pSG (STRATAGENE), pSVK3, pBPV, pMSG, pSVL (PHARMACIA). However, any other vector may be used as long as it is replicable and viable in the host.

The polynucleotide sequence, preferably the DNA sequence in the vector is operatively linked to an appropriate expression control sequence(s) (promoter) to direct mRNA synthesis. As representative examples of such promoters, one can mentioned prokaryotic or eukaryotic promoters such as CMV immediate early, HSV thymidine kinase, early and late SV40, LTRs from retrovirus, and mouse metallothionein-I. The expression vector also contains a ribosome binding site for translation initiation and a transcription vector. The vector may also include appropriate sequences for amplifying expression. In addition, the vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

As used herein, the term "host cell genetically engineered" relates to host cells which have been transduced, transformed or transfected with the polynucleotide or with the vector described previously. As representative examples of appropriate host cells, one can cites bacterial cells, such as *E. coli, Streptomyces, Salmonella typhimurium*, fungal cells such as yeast, insect cells such as Sf9, animal cells such as CHO or COS, plant cells, etc. The selection of an appropriate host is deemed to be within the scope of those skilled in the art from the teachings herein. Preferably, said host cell is an animal cell, and most preferably a human cell.

The introduction of the polynucleotide or of the vector described previously into the host cell can be effected by method well known from one of skill in the art such as calcium phosphate transfection, DEAE-Dextran mediated transfection, or electroporation. The composition of the invention may comprise one or more additives (e.g., stabilizers, preservatives). See, generally, *Ullmann's Encyclopedia of Industrial Chemistry*, 6th Ed. (various editors, 1989-1998, Marcel Dekker); and *Pharmaceutical Dosage Forms and Drug Delivery Systems* (ANSEL et al., 1994, WILLIAMS & WILKINS).

In a further aspect, the present invention provides a use, for treating and/or preventing a neurodegenerative disorder, of a compound selected in the group comprising:
  (i) a polypeptide comprising an amino acid sequence selected in the group comprising the amino acid sequence of the short isoform in *Homo sapiens* of the RdCVF2 gene (SEQ ID NO:1), orthologs, derivatives and fragments thereof;
  (ii) a polynucleotide coding for said polypeptide;
  (iii) a vector comprising said polynucleotide; and
  (iv) a host cell genetically engineered expressing said polypeptide.

In a further aspect, the present invention provides a use, for treating and/or preventing a neurodegenerative disorder, of a compound selected in the group comprising:
  (v) a polypeptide comprising an amino acid sequence selected in the group comprising the amino acid sequence of the long isoform in *Homo sapiens* of the RdCVF2 gene (SEQ ID NO:10), orthologs, derivatives and fragments thereof;
  (vi) a polynucleotide coding for said polypeptide;
  (vii) a vector comprising said polynucleotide; and
  (viii) a host cell genetically engineered expressing said polypeptide.

Typically, the medicament may be used for the therapeutic or prophylactic treatment of a subject, said subject corresponding to a mammal, in particular to a human.

As used herein, the expression "neurodegenerative disorder" refers to a disease associated with the degeneration of neurons such as degenerative disorders of the central nervous system, preferably implying Purkinje cells degeneration, degenerative disorders of the photoreceptors, or degenerative disorders of the olfactory neurons. As an example of degenerative disorders of the central nervous system, one can cite Alzheimer's Disease, Parkinson's Disease, and Huntington's Disease/Chorea. As an example of degenerative disorders of the photoreceptors, one can cite cone dystrophy (e.g., retinitis pigmentosa). As an example of degenerative disorders of olfactory neurons, one can cite anosmia. Said polypeptide, polynucleotide, vector, and host cell are as described previously. According to a preferred embodiment, said medicament may be used for treating and/or preventing degenerative disorders of the photoreceptors or degenerative disorders of the olfactory neurons.

There is also provided a method of preventing and/or treating a neurodegenerative disease comprising providing, to a subject displaying or predicted to display a neurodegenerative disorder, an effective amount of a composition comprising a compound selected in the group comprising:
  (i) a polypeptide comprising an amino acid sequence selected in the group comprising the amino acid sequence of the short isoform in *Homo sapiens* of the RdCVF2 gene (SEQ ID NO:1), orthologs, derivatives and fragments thereof;
  (ii) a polynucleotide coding for said polypeptide;
  (iii) a vector comprising said polynucleotide; and
  (iv) a host cell genetically engineered expressing said polypeptide.

According to the present invention, an "effective amount" of a composition is one which is sufficient to achieve a desired biological effect, in this case increasing the neuron viability. It is understood that the effective dosage will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the preferred dosage can be tailored to the individual subject, as is understood and determinable by one of skill in the art, without undue experimentation. Said polypeptide, polynucleotide, vector, and host cell are as described previously.

There is also provided a method of testing a subject thought to have or be predisposed to having a neurodegenerative disorder, which comprises the step of analyzing a biological sample from said subject for:
  (i) detecting the presence of a mutation in the RdCVF2 gene and/or its associated promoter, and/or
  (ii) analyzing the expression of the RdCVF2 gene.

As used herein, the term "biological sample" refers to any sample from a subject such as blood or serum. As used herein, the expression "neurodegenerative disorder" refers to a disease associated with the degeneration of neurons such as degenerative disorders of the central nervous system, degenerative disorders of the photoreceptors, or degenerative disorders of the olfactory neurons. Preferably, neurodegenerative disorder is a degenerative disorder of the photoreceptors such as cone dystrophy (e.g., retinitis pigmentosa).

Typical techniques for detecting a mutation in the RdCVF2 gene may include restriction fragment length polymorphism, hybridisation techniques, DNA sequencing, exonuclease reistance, microsequencing, solid phase extension using ddNTPs, extension in solution using ddNTPs, oligonucleotide assays, methods for detecting single nucleotide polymorphism such as dynamic allele-specific hybridisation, ligation chain reaction, mini-sequencing, DNA "chips", allele-specific oligonucleotide hybridisation with single or dual-labelled probes merged with PCR or with molecular beacons, and others. Analyzing the expression of the RdCVF2 gene may be assessed by any of a wide variety of well-known methods for detecting expression of a transcribed nucleic acid or translated protein. In a preferred embodiment, the expression of the RdCVF2 gene is assessed by analyzing the expression of mRNA transcript or mRNA precursors, such as nascent RNA, of said gene. Said analysis can be assessed by preparing mRNA/cDNA from cells in a biological sample from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TaqMan), and probes arrays such as GeneChip™ DNA Arrays (AFFYMETRIX).

Advantageously, the analysis of the expression level of mRNA transcribed from the RdCVF2 gene involves the process of nucleic acid amplification, e.g., by RT-PCR (the experimental embodiment set forth in U.S. Pat. No. 4,683, 202), ligase chain reaction (BARANY, *Proc. Natl. Acad. Sci. USA*, vol. 88, p: 189-193, 1991), self sustained sequence replication (GUATELLI et al., *Proc. Natl. Acad. Sci. USA*, vol. 87, p: 1874-1878, 1990), transcriptional amplification system (KWON et al., 1989, *Proc. Natl. Acad. Sci. USA*, vol. 86, p: 1173-1177, 1989), Q-Beta Replicase (LIZARDI et al., *Biol. Technology*, vol. 6, p: 1197, 1988), rolling circle replication U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

In view of the present application, one of skill in the art can simply identify the sequence of the gene RdCVF2 in a subject. As an example, the sequence of the cDNA coding for the short isoform of RdCVF2 in *Homo sapiens* has the sequence SEQ ID NO.11.

In another preferred embodiment, the expression of the RdCVF2 gene is assessed by analyzing the expression of the protein translated from said gene. Said analysis can be assessed using an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin)), or an antibody fragment (e.g., a single-chain antibody, an isolated antibody hypervariable domain, etc.) which binds specifically to the protein translated from the RdCVF2 gene. Said analysis can be assessed by a variety of techniques well known from one of skill in the art including, but not limited to, enzyme immunoassay (EIA), radioimmunoassay (RIA), Western blot analysis and enzyme linked immunoabsorbant assay (RIA).

Polyclonal antibodies can be prepared by immunizing a suitable animal, such as mouse, rabbit or goat, with a protein encoded by the RdCVF2 gene or a fragment thereof. The antibody titer in the immunized animal can be monitored over time by standard techniques, such as with an enzyme linked immunosorbent assay (ELISA) using immobilized polypeptide. At an appropriate time after immunization, e.g., when the specific antibody titers are highest, antibody producing cells can be obtained from the animal and used to prepare monoclonal antibodies (mAb) by standard techniques, such as the hybridoma technique originally described by KOHLER and MILSTEIN (*Nature*, vol. 256, p: 495-497, 1975), the human B cell hybridoma technique (KOZBOR et al., *Immunol.*, vol. 4, p: 72, 1983), the EBV-hybridoma technique (COLE et al., *In Monoclonal Antibodies and Cancer Therapy*, Alan R. Liss, Inc., p: 77-96, 1985) or trioma techniques. The technology for producing hybridomas is well known (see generally Current Protocols in Immunology, COLIGAN et al. ed., John Wiley & Sons, New York, 1994). Hybridoma cells producing the desired monoclonal antibody are detected by screening the hybridoma culture supernatants for antibodies that bind the polypeptide of interest, e.g., using a standard ELISA assay.

The method of the invention may comprise comparing the level of expression of the RdCVF2 gene in a biological sample from a subject with the normal expression level of said gene in a control. A significantly weaker level of expression of said gene in the biological sample of a subject as compared to the normal expression level is an indication that the patient has or is predisposed to developing a neurodegenerative disorder. The "normal" level of expression of the RdCVF2 gene is the level of expression of said gene in a biological sample of a subject not afflicted by any neurodegenerative disorder, preferably not afflicted with retinis pigmentosa. Preferably, said normal level of expression is assessed in a control sample (e.g., sample from a healthy subject, which is not afflicted by any neurodegenerative disorder) and preferably, the average expression level of said gene in several control samples.

In the following, the invention is described in more detail with reference to amino acid sequences, nucleic acid sequences and the examples. Yet, no limitation of the invention is intended by the details of the examples. Rather, the invention pertains to any embodiment which comprises details which are not explicitly mentioned in the examples herein, but which the skilled person finds without undue effort.

EXAMPLES

1) Identification of RdCVF2, a Gene Paralogous to RdCVF

The mouse RdCVF gene is located on chromosome 8 and contains three exons and can be transcribed in two distinct splice variants corresponding to RdCVF-L (long) and RdCVF-S (short) respectively. The structure of both RdCVF splice variants is described in FIG. 1, panel a. The RdCVF-L mRNA (NM_145598, mouse chromosome 8, minus strand, from 70'033'763 to 70'027'717) is composed of three exons (1-3) of 348, 687 and 1751 bp. The RdCVF-S mRNA (BC017153, from 70'033'785 to 70'032'615) is composed of one exon (1172 bp). Coding and non-coding regions are depicted in dark grey) and light grey respectively. The genomic region surrounding the stop codon at the end of the first coding exon and the corresponding orthologous sequences in 12 other vertebrate genomes are aligned. The black triangles indicate the end of the first RdCVF-L coding exon. Conserved stop codons are colored in red. At bottom, lengths of the coding (CDS) and terminal untranslated regions (UTR) are given.

The RdCVF-L splice variant is composed of three exons, which variant codes for a protein wherein the last 109 amino acids are called the "cap". The RdCVF-S splice variant is composed of a single exon in which the coding sequence is the same as the first exon of the long form extended by one codon followed by a stop codon (TGA) and finally a 3' untranslated region (UTR). Consequently, the "cap" (i.e., the last 109 amino acids) of RdCVF-L are missing in RdCVF-S.

A blast search on databases enabled the identification of a paralogous gene called RdCVF2. The structure of both RdCVF2 splice variants is described in FIG. 1, panel b. The RdCVF2-L mRNA (AK015847, mouse chromosome 13, plus strand, from 50'202'630 to 50'206'797) is composed of two exons (1-2) of 603 and 564 bp. The RdCVF2-S mRNA (BC016199, from 50'202'667 to 50'205'571) is composed of one exon (2904 bp). Coding and non-coding regions are depicted in dark grey) and light grey respectively. The genomic region surrounding the stop codon at the end of the first coding exon and the corresponding orthologous sequences in 12 other vertebrate genomes are aligned. The black triangles indicate the end of the first RdCVF2-L coding exon. Conserved stop codons are colored in red. At bottom, lengths of the coding (CDS) and terminal untranslated regions (UTR) are given.

This analysis enables to locate RdCVF2 gene on chromosome 13 and to demonstrate that RdCVF and RdCVF2 sequences and gene structures are highly similar between both. In fact, it appears that RdCVF2 also encodes both a thioredoxin-like protein (156 aa, SEQ ID NO.12) and a shorter form (101 aa, SEQ ID NO.2) called RdCVF2-L and RdCVF2-S respectively. Finally, the sequence analysis has revealed that the degree of homology between RdCVF and RdCVF2 is 58.0% for the long isoforms and 53.5% for the short isoforms.

2) Conservation of RdCVF and RdCVF2 Gene Structure During Evolution

Cone viability is related to the production of the RdCVF-S form and, by extension, to the presence of the stop codon at the end of the first exon required to obtain that isoform. To evaluate conservation of that stop codon further, the UCSC genome browser BLAT (HINRICHS et al., *Nucleic Acids Res.*, vol. 34 (Database issue): D590-598, 2006; KENT, *Genome Res.*, vol. 12(4), p: 656-664, 2002) server was used to map the mouse RdCVF and RdCVF2 genes to all the available vertebrate genomes and to extract the corresponding genomic sequences.

The results have shown that both loci were found in 13 vertebrates. All these organisms exhibited both genes except *Takifugu rubripes* and *Tetraodon nigroviridis*, in which RdCVF was duplicated at the same chromosomal location (RdCVF a and b) with an additional intron inserted into the first coding exon of this loci. It is noteworthy that the stop codon at the end of the first exon is strictly conserved in the vast majority (FIG. 1, panel a and b). Finally, this observation implies the possible existence of RdCVFs short isoforms in most vertebrates, excepting *Gallus gallus* and *Brachydanio rerio* RdCVF; *Tetraodon nigroviridis* and *Takifugu rubripes* RdCVFb.

3) Analysis of RdCVF and RdCVF2 Protein Sequences

In order to identify candidate RdCVF and RdCVF2 orthologous proteins, homology searches in the UniProt (WU et al., *Nucleic Acids Res.*, vol. 34 (Database issue), p: D187-191, 2006) and EMBL (COCHRANE et al., *Nucleic Acids Res.*, vol. 34 (Database issue), p: D10-15, 2006) public sequence databases were performed using the BLAST programs (ALTSCHUL et al., *J. Mol. Biol.*, vol. 215(3), p: 403-410, 1990; ALTSCHUL et al., *Nucleic Acids Res.*, vol. 25(17), p: 3389-3402, 1997). Proteins orthologous to RdCVF(-L/2-L) referring to the long isoforms of both RdCVF genes, were identified or predicted in vertebrates (*Rattus norvegicus, Homo sapiens, Pan troglodytes, Bos taurus, Canis familiaris, Gallus gallus, Xenopus laevis, Tetraodon nigroviridis, Brachydanio rerio*) according to protein or genome database searches. Then, TBA (BLANCHETTE et al., *Genome Res.*, vol. 14(4), p: 708-715, 2004) and PipeAlign (PLEWNIAK et al., *Nucleic Acids Res.*, vol. 31(13), p: 3829-3832, 2003) programs were used with default parameters to generate the multiple alignments of genomic and protein sequences respectively. Protein alignment occasionally included manual adjustments in keeping with the protein secondary structure conservation.

Figure 2A:
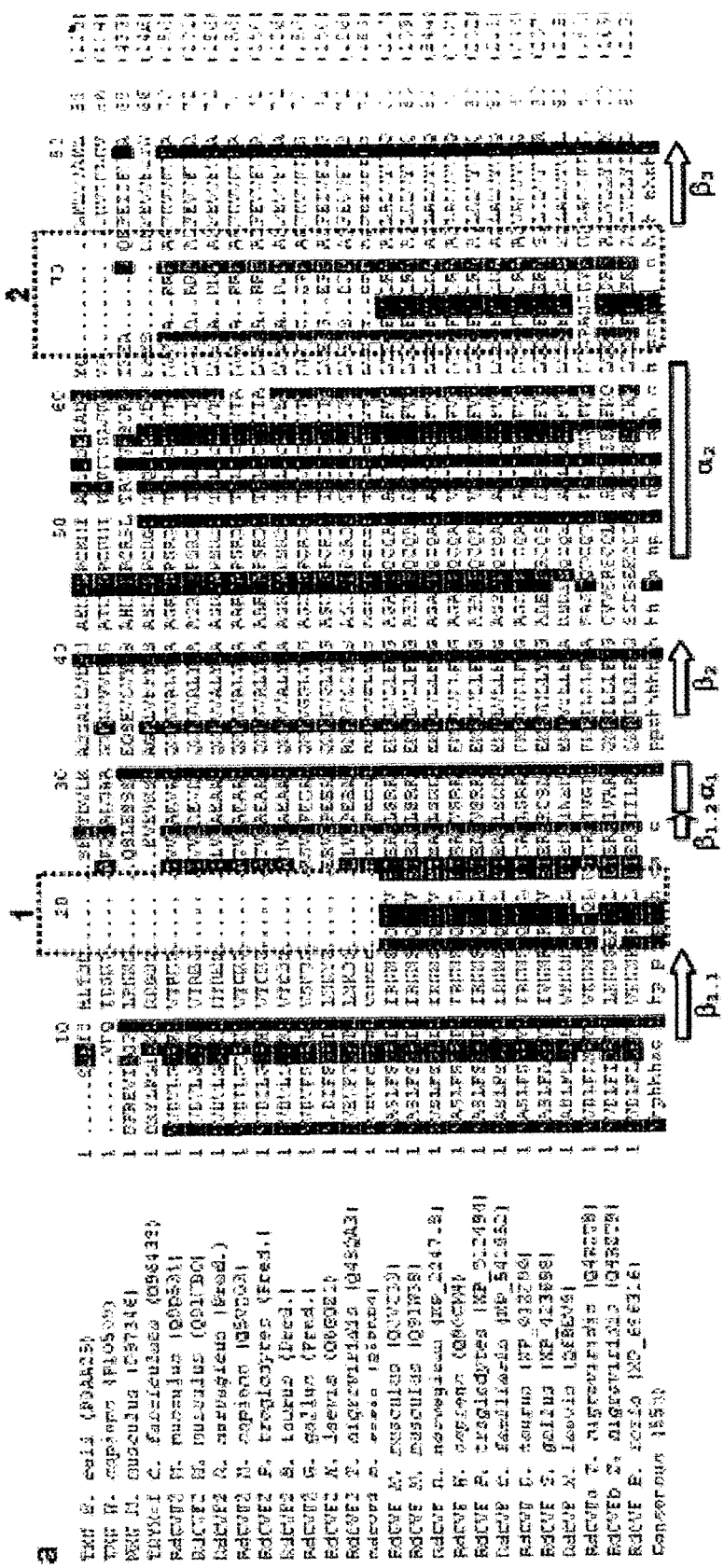
FIG. 2 shows the Sequence and structure similarities of mouse RdCVF and RdCVF2 proteins with thioredoxin superfamily members.
Figure 2B:
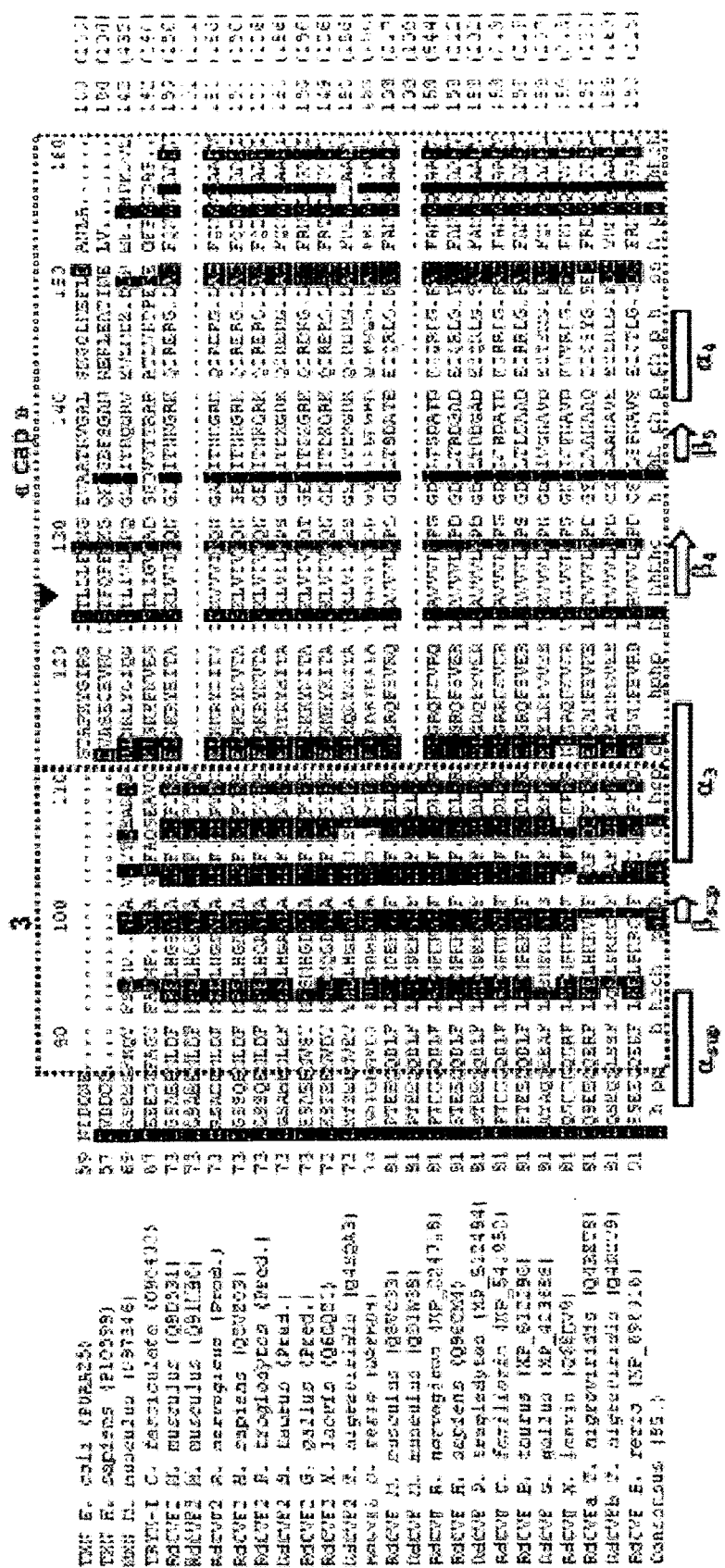
Figure 2C:
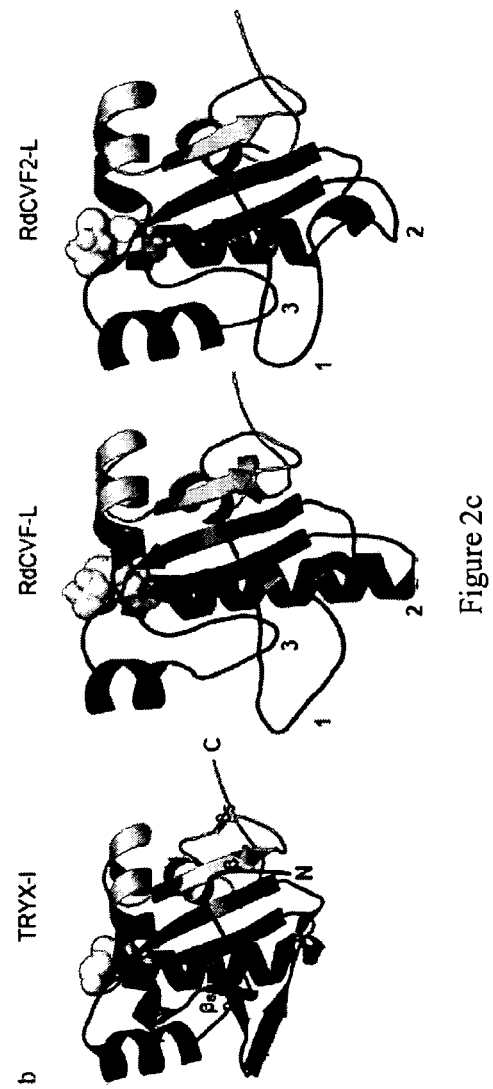

The FIG. 2 (panel a) show the sequences alignment of RdCVF, RdCVF2, tryparedoxin (TRYX), nucleoredoxin (NXN) and thioredoxin (TXN). The name, organism and accession number (in brackets) of each protein sequence are given (left). Identical (white text on black) small (A, D, G, P, S, T; white text on green) hydrophobic (A, C, F, G, I, L, M, S, T, V, W, Y; black text on yellow) polar (D, E, H, K, N, Q, R, S; blue text) and charged (D, E, K, R; white text on red) conserved residues are shown according to a conservation threshold of 85%. A consensus sequence is given below the multiple alignments in which s, h, p and c correspond to small, hydrophobic, polar and charged residues respectively. The secondary structures (β sheet and α helix) of the *Crithidia fasciculata* tryparedoxin I structure (1 EWX) are given below the consensus sequence. The blue dashed rectangles indicate the three RdCVF(2) specific insertions. The green dashed rectangle shows the "cap"

region absent in RdCVF(2)-S. The position of the human thioredoxin cleavage product (TRX80) is indicated (red triangle). Panel b displays the structure of the *Crithidia fasciculata* TRYX-I (1 EWX) (left) mouse RdCVF-L (center) and mouse RdCVF2-L (right) models. Regions of TRYX-I backbone conserved in RdCVF(2)-L are colored in red. The "cap" region and the three specific insertions are depicted in green and blue respectively. The putative catalytic site ($C_{44}XXC_{47}$) is shown in yellow with a space-filling representation.

A phylogenetic analysis among the TXN superfamily established that RdCVF and RdCVF2 proteins are closely related to the TRYX and NXN members (MICOSSI et al., *Acta Crystallogr. D. Biol. Crystallogr.*, vol. 58(Pt 1), p: 21-28, 2002; KRUMME et al., *Biochemistry*, vol. 42(50), p: 14720-14728, 2003; ALPHEY et al., *J. Biol. Chem.*, vol. 274(36), p: 25613-25622, 1999; EKLUND et al., *Proteins*, vol. 11(1), p: 13-28, 1991; KUROOKA et al., *Genomics*, vol. 39(3), p: 331-339, 1997; LAUGHNER et al., *Plant Physiol.*, vol. 118(3), p: 987-996, 1998). Even distant homologs such as *Crithidia fasciculata* tryparedoxin I (O96438, TRYX-I) (ALPHEY et al., 1999, abovementioned) exhibit 42.5% and 45.4% sequence similarity to mouse RdCVF(-L/2-L) proteins. Three insertions in the multiple alignment (called 1, 2 and 3) allow one to distinguish these phylogenetic protein families (FIG. 2, panel a).

Insertion 3 (residues 87-110) contains the conserved motif WLALP [$W_{108}(L,V)(A,F)(L,V,I)P_{112}$] and clearly discriminates the TRYX family [TRYX, NXN, RdCVF and RdCVF2] from TXN superfamily. Insertion 2 (63-72) and two additional residues (96-97) of insertion 3 allow one to differentiate the RdCVF and RdCVF2 proteins from the rest of the TRYX family. Finally, insertion 1 (16-21) unambiguously separates RdCVF from all the other TXN superfamily members including RdCVF2. It has to be noted that the thioredoxin active site $C_{44}XXC_{47}$ is only conserved in 44.4% (4/9) and 72.7% (8/11) of the RdCVF and RdCVF2 vertebrate proteins respectively.

4) Structural Modeling of RdCVF and RdCVF2

The high sequence similarity of RdCVFs with TRYX proteins prompted us to build the RdCVF(-L/2-L/-S/2-S) structural models with *Crithidia fasciculata* TRYX-I crystal structure (PDB accession number: 1 EWX, 1.7 Å resolution structure) (ALPHEY et al., 1999, abovementioned) as a template. By analogy with human TXN and TRX80 models (PEKKARI et al., 2000, abovementioned) the RdCVF(-S/2-S) structure models were assumed to maintain the same overall folding. Structural models for mouse RdCVF and RdCVF2 (both S and L forms) using the 155 and 147 first residues respectively were constructed using the Builder homology modeling package (KOEHL and DELARUE, *J. Mol. Biol.*, vol. 239(2), p: 249-275, 1994; KOEHL and DELARUE, *Nat. Struct. Biol.*, vol. 2(2), p: 163-170, 1995; KOEHL and DELARUE, *Curr. Opin. Struct. Biol.*, vol. 6(2), p: 222-226, 1996). The final models were further refined by energy minimization, using ENCAD (LEVITT et al., *Computer Physics Comm.*, vol. 91, p: 215-231, 1995). On each model 1000 steps of conjugate gradient minimization was applied. The $E_{146}(1EWX) \rightarrow P_{146}$(RdCVF-L) mutation obliges the local backbone conformation in the template structure to be adapted to fit the proline. Builder samples simultaneously the conformation of the loops in the five insertions/deletions and in the E→P mutation region, and the conformation of the side-chains, using a self consistent mean field approach. PyMOL (www.pymol.org) was used to render the final structures.

The Figure (panel b) show the structures of TRYX-I (1 EWX) and RdCVF(-L/2-L). FIG. 2 displays the 1 EWX secondary structures (β-sheet and α-helix) below the multiple alignment (panel a) and in the TRYX-I 3D-structure (panel b).

The structure modelization shows that insertions 1, 2 and 3 correspond respectively to: an increase in size of the $\beta_{1.1}$-$\beta_{1.2}$ sheets, a one turn extension in the $\alpha_2$ helix, and a larger structural region containing the TRYX-specific $\alpha_{sup}$-$\beta_{sup}$ and $\alpha_3$ extension. The two residues (96-97) belonging to insertion 3 in the RdCVF proteins correspond to a larger constrained loop before strand $\beta_{sup}$ and allow one to discriminate these proteins from TRYX members. It is worth noting that the location on the folded protein where the three insertions co-localize are on the opposite side from the putative catalytic site ($C_{44}XXC_{47}$) in RdCVFs (FIG. 2, panel b).

Finally, the C-terminal region absent in RdCVF(-S/2-S) proteins (hereafter called "cap" and depicted in green in FIG. 2, panel b) is positionally fixed relative to the catalytic site. The "cap" region in TXN proteins interacts with the recycling enzyme thioredoxin reductase [7, 13] and its absence might impair the thioredoxin activity in TRX80 and RdCVF(-S/2-S) [4, 13].

A striking feature of these structural models is the clear spatial proximity of residues from the three insertions. This coincidence points to a possibly novel interaction site in RdCVF(-L/2-L). As expected, the backbone conformation of the refined model of RdCVF(-S/2-S) is the same as its counterpart in the long forms, with minor modifications observed in the side-chains at the interface between the non-"cap" and "cap" regions. It should be emphasized that the absence of the "cap" yields to the emergence of a major hydrophobic patch at the RdCVF(-S/2-S) surface. As a consequence the hydrophobic part of the accessible surface area of RdCVF proteins increases from 2394 Å$^2$ in the long form to 3157 Å$^2$ in the short form.

5) RdCVF-S, RdCVF2-S and RdCVF2-L are Expressed in the Retina in a Rod-Dependent Manner Total RNA from neural retina of 8, 15 and 35-day-old wild type (C57BL/6@N), and rd1 mutant, (C3H/He@N) mice and from olfactory epithelium (Balb/c) was purified by cesium gradient (CHIRGWIN et al., *Biochemistry*, vol. 18(24), p: 5294-5299, 1979). Double-stranded cDNA was synthesized from 5 µg total RNA using Superscript Choice System (Invitrogen). cDNAs were produced by random priming and normalized according to glucose-6-phosphate dehydrogenase (GAPDH) mRNA. First strand cDNA (0.2 µl) was amplified in triplicate using 2 µM of the specific primers. Primers 5'-CATCACCAACAAAGGGCGGAAG-3' (SEQ ID NO.13) and 5'-CATTCCTCAGCAGA-GAAGGGAAC-3' (SEQ ID NO.14) were used for RdCVF2-S; primers 5'-CCGTGCTATTGTTTCAGAGC-CCTTAACTTTCTATC-3' (SEQ ID NO.15) and 5'-CT-GACACTCCAATCGTAAAAGGCAGAAAACGC-3' (SEQ ID NO.16) were used for RdCVF2-L. Primers 5'-AAGCCGATGAGCAACTTCC-3'(SEQ ID NO.17) and 5'-TCATCTCCCAGTGGATTCTT-3' (SEQ ID NO.18) were used for rhodopsin on a lightcycler (Roche, Basel, Switzerland).

For northern blotting analysis, 2 µg of poly-A mRNA was used and the membrane was hybridized to a probe corresponding to exon 1 of the RdCVF2 gene using standard method. The absence of DNA contamination was checked by omitting the reverse transcriptase. Results are displayed as fold difference compared to the lowest expression.

Figure 3:
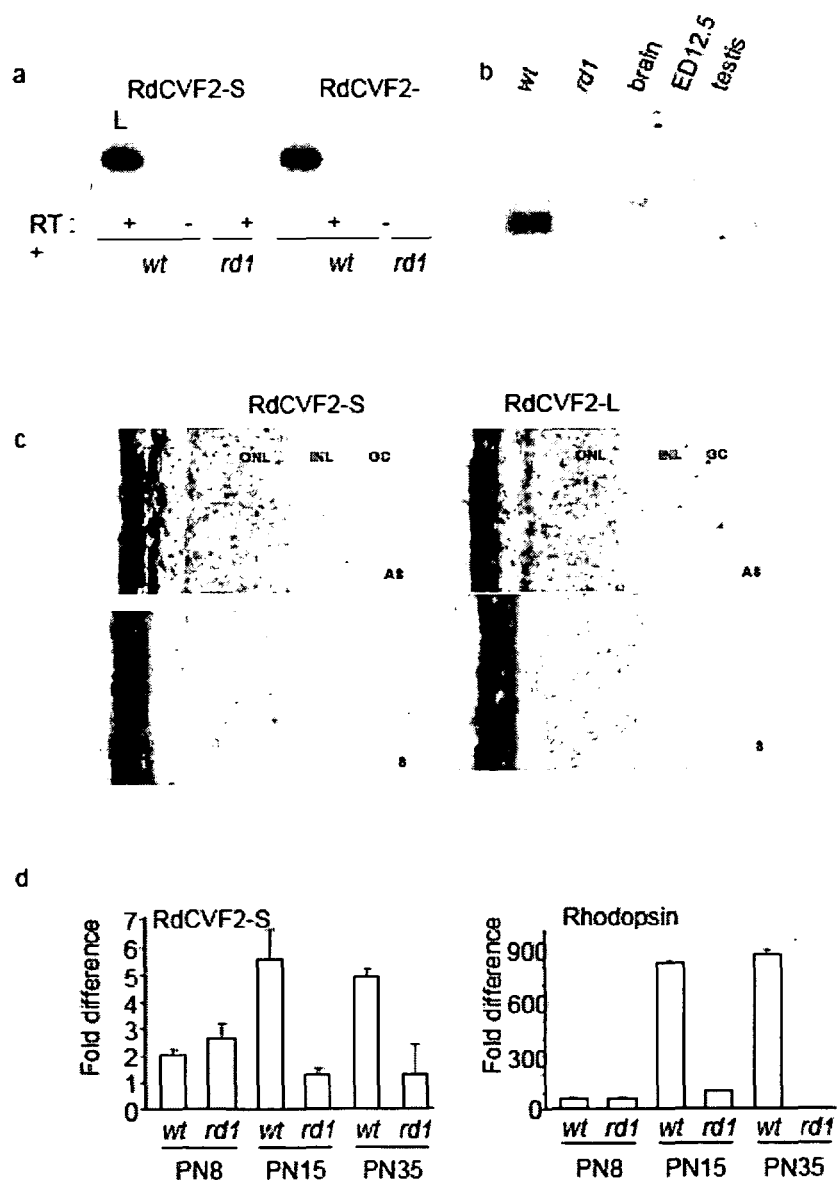
FIG. 3 shows the validation of the RdCVF2 expression in retina.

The FIG. 3, panel a show the results of RT-PCR on wild type and rd1 mice retina at post-natal day 35 for the short (RdCVF2-S, 176 pb fragment) and long (RdCVF2-L, 170 pb fragment) isoforms of RdCVF2. The FIG. 3, panel b shows the expression of RdCVF2 transcripts in brain, testis, normal retina (wt), degenerated retina (rd1) and in the whole mouse embryo at embryonic day 12.5 (ED12.5).

The results established that RdCVF2-S and -L are expressed in the wild-type mouse retina (FIG. 3, panel a). Interestingly, RdCVF2-S and -L expression was absent in the retina of the rd1 mouse after rod-photoreceptor degeneration. The results also show that in addition to the expression in the retina, most likely by rod photoreceptors since its expression is absent in the degenerated retina (rd1), a weaker expression of RdCVF2 is observed in the brain and testis. Moreover, the results have shown that an expression of the two messengers RNA corresponding to the short (RdCVF2-S) and the long (RdCVF2-L) isoforms is also detected in the olfactory epithelium. Finally, no expression was detected in the whole mouse embryo at embryonic day 12.5. The expression of RdCVF2-S and -L mRNA in the retina and in the olfactory epithelium was analyzed by in situ hybridization with a digoxigenin (DIG)-labeled murine antisense riboprobe.

Mouse RdCVF2-S and RdCVF2-L was amplified by PCR using the following primers: primers 5'-GTAGCTTTG-TACTTTGCGGCG-3' (SEQ ID NO.19) and 5'-GTCATCA-GAAAATGTATCACCTCCATAGG-3' (SEQ ID NO.20) for RdCVF2-S; primers 5'-GCCATCTCTGCGACTTATTTT-TACC-3' (SEQ ID NO.21) and 5'-AATTAGTGCCACCA-GCACCATC-3' (SEQ ID NO.22) for RdCVF2-L. The PCR product was cloned into PGEM easy vector (Promega). Sense and antisense RdCVF2 mRNA probes generated from SP6 or T7 promoters and labeled with digoxigenin-UTP (ROCHE) were generated according to manufacturer's instruction.

After defrosting and drying at room temperature, retina and olfactory epithelium sections were post-fixed on ice for 10 min in 4% paraformaldehyde washed in PBS at room temperature for 10 min. retina sections were hybridized with sense and antisense RdCVF2 mRNA probes generated from SP6 or T7 promoters and labeled with digoxigenin-UTP. In situ hybridization and digoxigenin-labeled probe detection were performed as described previously (ROGER et al., Dev. Biol., vol. 298(2), p: 527-539, 2006). The specificity of the staining was demonstrated by the lack of hybridization signal with the sense probe.

The FIG. 3, panel c shows the results of In situ hybridization on sections of wild-type and rd1 mice retina with digoxigenin-labeled RdCVF2-S and L riboprobes (AS: antisens, S: sens). Original magnification: 40×. The results show that the transcripts for RdCVF2-S and -L were detected in the photoreceptor layer. No staining was observed with the sense control probes, supporting the specificity of the RdCVF2-S and L probes. Finally, no expression was detected in the rd1 retina after rod degeneration (result not shown). Moreover, the results have shown that the localisation of labelled cells in olfactory epithelium suggests that basal cells, immature and mature neurons strongly express RdCVF2 mRNA, and that no expression of RdCVF2 mRNA was observed at the apical position of the cytoplasm of the supporting cells. It must be noted that a small expression of RdCVF2 mRNA was also observed during development (E12.5) specifically restrictive to the nasal development. Finally, the expression of RdCVF2-S and of RdCVF2-L were analysed during the process of rod degeneration.

The FIG. 3, panel d show the expression time-courses of both RdCVF2 isoforms and rhodopsin transcripts in wild type (wt) and rd1 mice at post natal day 8, 15 and 31 (PN8, PN15 and PN35). The results established that at post-natal day 8 (PN8) before the onset of rod loss, RdCVF2-S is expressed at similar level in the wild-type and in the rd1 retina similarly to the rod photopigment gene rhodopsin. From PN15 to PN35, the degeneration of rods (measured by the decrease in rhodopsin expression) is correlated with a decrease in RdCVF2-S expression. Consequently, these results indicate that RdCVF2-S is expressed in a rod-dependent manner. The same results have been observed with RdCVF2-L (data not shown).

6) RdCVF2 mRNA is not Only Expressed in the Retina and in Olfactive Epithelium but Also in Other Tissues Mouse mRNA and EST sequences associated with both RdCVF and RdCVF2 isoforms (L and S) were used to estimate the tissue specificity of each messenger. The results are presented in the following table.

| Genes | isoform | mRNA and EST EMBL accession numbers | Expression location |
|---|---|---|---|
| RdCVF | L | BC021911; BI738445; CB849876; CK623520; BI731629; BI872244; BG294111; BI734135; BU505070; BU840744; BQ929742; BQ938066; BI73223; CK628091; BY742305; N539863; CO424399; BB277874; BB279867; CO426411 | Retina, RPE, choroid and/or eye |
| | | BF470336; BE983242; AW495183 | None |
| | S | BC017153; CB849876; BG299078; BY742292 | Retina and/or eye |
| RdCVF-2 | L | CK621895; CK620198; BG288447; BB282056; BB279962; BB281743; BB277718; BB277574; BB277714; BI732427 | Retina |
| | | BC038905; BI108740 | Mammary tumor, tumor and/or gross tissue |
| | | BY715393; AV266697 | Testis |
| | | DT906804 | Hematopoietic stem cells |
| | | BY435086 | amnion |
| | | AI324093 | Placenta |
| | | BB552115 | Oviduct |
| | | AA261233 | Foetus |
| | | BB241367 | Thymus |

-continued

| Genes | isoform | mRNA and EST EMBL accession numbers | Expression location |
|---|---|---|---|
| | | AI536471 | Mammary gland |
| | | BX632214; BF460609; BX514476 | |
| | S | BC016199; BG297304; BG297383 | Retina |
| | | BX514476 | None |

Figure 4:
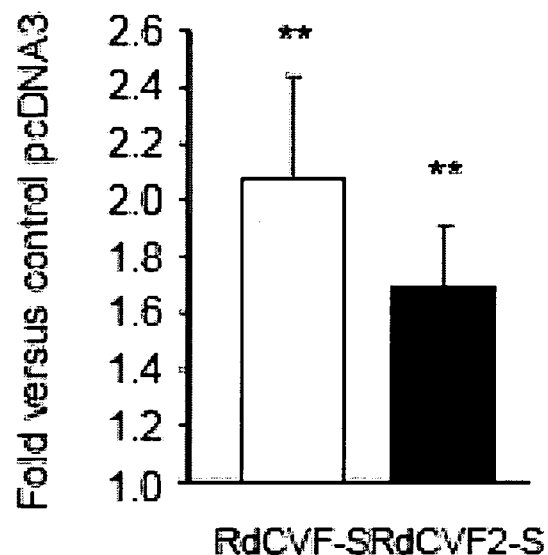
FIG. 4 shows the cone viability assay in the presence of RdCVF-S and RdCVF2-S.

As reported before (LEVEILLARD et al., 2004, abovementioned), the results confirmed that RdCVF-L and RdCVF-S mRNAs are specifically expressed in eye and retina as 20/23 and 4/4 sequences were found in these tissues respectively. The results show that mouse RdCVF2-L mRNA is also preferentially expressed in retina (10/24) but is also present in other tissue types such as tumor (2), testis (2), stem cells (2), amnion (1), placenta (1), oviduct (1), foetus (1), thymus (1), and mammary gland (1). These results confirmed the expression of RdCVF2 observed in the testis and brain (FIG. 4, panel b). Finally, EST and mRNA sequences corresponding to RdCVF2-S are exclusively expressed in retina (3/4).

7) RdCVF2 Cone Viability Effects

The strong similarities between RdCVF and RdCVF2 loci in terms of gene organization, conservation of sequence and rod-dependent expression led us to hypothesize that RdCVF2 protein might also be able to promote cone viability as previously reported for RdCVF-S (LEVEILLARD et al., 2004, abovementioned). RdCVF(-S/2-S/2-L) isoforms were cloned into the expression plasmid pcDNA3 and transfected into COS-1 cells. 48 hours after transfection, the conditioned media from the COS-transfected cells was harvested and incubated with a cone-enriched primary cell culture system from chicken embryo (60-80% of cones) (FINTZ et al., *Invest. Opthalmol. Vis. Sci.*, vol. 44(2), p: 818-825, 2003).

After seven days of incubation, a period over which these post-mitotic cells degenerate, the viability of the cells in the culture was scored using the Live/Dead assay (MOLECULAR PROBES) and a cell counting platform as previously described [4]. The viability corresponding to three independent assays is represented as fold over pcDNA3 used as negative control. The FIG. 4 shows the rescue activity of RdCVF-S and RdCVF2-S when compared to that of empty vector (pcDNA3). Statistical analysis (Tuckey test) shows that the results are statistically significant ($p<0.001$).

The results show that the number of live cells in the presence of RdCVF-S is twice than the control (pcDNA3). A less pronounced, but statistically significant, increase in cone viability (1.6 fold) is observed for RdCVF2-S. These findings confirm that RdCVF2-S is also a cone viability factor similar to RdCVF-S (LEVEILLARD et al., 2004, abovementioned). Importantly, no synergistic trophic effect on cones is observed when both RdCVF-S and RdCVF2-S are co-tranfected in COS-1 cells pointing to use of the same pathway by both factors (data not shown).

8) RdCVF2 OSN Viability Effects

Since RdCVF2 is also expressed in olfactory neurons, the possible viability activity of RdCVF2 on culture of Olfactory Sensitive Neurons (OSN) has been analysed. Adult mice were killed by decapitation. The posterior part of the nasal septum was dissected free of the nasal cavity and immediately placed in ice-cold Dulbecco's modified Eagle's medium (DMEM) containing 50 µg/ml gentamicin (EUROBIO; GIBCO) and 10% (v/v) fetal calf serum (EUROBIO).

The cartilage of the septum was removed and the olfactory mucosa was incubated for 30 min at 37° C. in a 2.4 units/ml dispase II solution (ROCHE). The olfactory epithelium was carefully separated from the underlying lamina propria under the dissection microscope and was gently triturated about 20 times to separate the cells. The resulting cell suspension was transferred to a 50 ml conical tube and the dispase was inactivated by adding 40 ml of HBSS without Calcium and magnesium. The cell suspension was centrifuged at 700 rpm for 5 min. The supernatant was aspirated and the pellet containing the cells was resuspended in a medium composed of DMEM containing insulin (10 µg/ml, SIGMA), transferin (10 µg/ml, SIGMA), selenium (10 µg/ml, SIGMA), calf foetal serum (5%), ascorbic acid (200 µM,). Cells were plated at the density of cells/cm2 on 12 mm sterile glass coverslips coated with 5 µg/cm2 human collagen IV (SIGMA).

Figure 5:
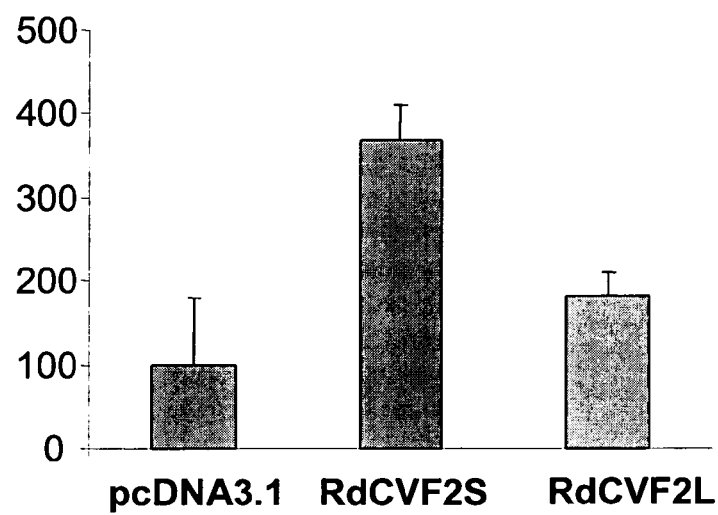
FIG. 5 shows the cell viability assay of Olfactory Sensitive Neurons (OSN) in the presence of RdCVF-S and RdCVF2-S.

Expression vectors encoding for RdCVF(-S/2-S/2-L) isoforms described previously were transfected into COS-1 cells. 48 hours after transfection, the conditioned media from the COS-transfected cells was harvested and incubated with the culture of OSN. After 4 days of culture, cells were fixed and labelled with tubulin III, and counted. The results shown in FIG. 5 have established that the OSN cell viability was more important in the presence of the RdCVF2-S isoform compared to control. Protective effects were observed with RdCVF2-L.

9) RdCVF2 Purkinje Cells Viability Effects

After decapitation of mouse at postnatal day 1-3, brains were dissected out into cold Gey's balanced salt solution containing 5 mg/ml glucose, and meninges were removed. Cerebellar parasagittal slices (350 or 250 µm thick) were cut on a McIlwain tissue chopper and transferred onto membranes of 30 mm MILLIPORE culture inserts with 0.4 µm pore size (MILLICELL; MILLIPORE, Bedford, Mass.). Slices were maintained in culture in six-well plates containing 1 ml or in 10 cm culture dishes containing 3 ml of medium at 35° C. in an atmosphere of humidified 5% CO2. The medium was composed of 50% basal medium with Earle's salts (INVITROGEN), 25% HBSS (INVITROGEN), 25% horse serum (INVITROGEN), L-glutamine (1 mM), and 5 mg/ml glucose (Stoppini et al., *J. Neurosci. Methods.*, vol. 37(2), p: 173-82, 1991).

Expression vectors encoding for RdCVF(-S/2-S/2-L) isoforms described previously were transfected into COS-1 cells. 48 hours after transfection, the conditioned media from the COS-transfected cells was harvested and incubated with the culture of purkinje cells. After 4 days of culture, cells were fixed and counted.

10) RdCVF2 Cortical Neurons Viability Effects

Serum-free preparation of mouse cortical primary cultures was performed with mouse at postnatal day 1. After removal of meninges, entire cortices were mechanically dissociated in a phosphate buffer saline glucose solution without added divalent cations (100 mM NaCl, 3 mM KCl, 1.5 mM KH2PO4, 7.9 mM Na2HPO4, 33 mM glucose, 100

U/ml penicillin and 100 µg/ml streptomycin) and resuspended in Neurobasal-medium (GIBCO-INVITROGEN) containing 2% B27 supplement (GIBCO), 0.5 mM glutamine, and 25 µM glutamate. Cells were then cultured onto poly-ornithine-coated coverslips to produce cultures highly enriched in neurons.

Expression vectors encoding for RdCVF(-S/2-S/2-L) isoforms described previously were transfected into COS-1 cells. 48 hours after transfection, the conditioned media from the COS-transfected cells was harvested and incubated with the culture of cortical neurons. After 4 days of culture, cells were fixed and counted. Finally, the results established that a novel trophic factor for cone survival, and more generally for neuron survival has been identified. This factor defines a novel family of bifunctional proteins with potential involvement in neuroprotection and response to oxidative stress.

The invention claimed is:

1. A method for treating cone dystrophy comprising the administration of an effective amount of a polypeptide comprising the amino acid sequence of long isoform in *Homo sapiens* of the RdCVF2 gene, and having the sequence set forth in SEQ ID NO:10, to a patient in need thereof.

* * * * *